US010934152B2

(12) United States Patent
Swears

(10) Patent No.: US 10,934,152 B2
(45) Date of Patent: Mar. 2, 2021

(54) FLUID DISPENSER

(71) Applicant: Greg Swears, Spring Lake, MI (US)

(72) Inventor: Greg Swears, Spring Lake, MI (US)

(*) Notice: Subject to any disclaimer, the term of this patent is extended or adjusted under 35 U.S.C. 154(b) by 300 days.

(21) Appl. No.: 15/945,513

(22) Filed: Apr. 4, 2018

(65) Prior Publication Data
US 2018/0290875 A1 Oct. 11, 2018

Related U.S. Application Data

(60) Provisional application No. 62/482,981, filed on Apr. 7, 2017.

(51) Int. Cl.
B67D 3/00 (2006.01)
A47J 36/24 (2006.01)
A61M 1/06 (2006.01)
B67D 1/04 (2006.01)
B65D 47/24 (2006.01)

(52) U.S. Cl.
CPC ........ *B67D 3/0022* (2013.01); *A47J 36/2433* (2013.01); *A61M 1/064* (2014.02); *B67D 1/0462* (2013.01); *B67D 3/007* (2013.01); *B67D 3/0035* (2013.01); *B67D 3/0067* (2013.01); *B67D 3/0083* (2013.01); *B65D 47/243* (2013.01); *B67D 1/04* (2013.01); *B67D 2210/00031* (2013.01); *B67D 2210/00118* (2013.01)

(58) Field of Classification Search
CPC .. B67D 3/0022; B67D 1/0462; B67D 3/0035; B67D 3/0067; B67D 3/007; B67D 3/0083; B67D 1/04; A61M 1/064; A47J 36/2433; B65D 47/243

See application file for complete search history.

(56) References Cited

U.S. PATENT DOCUMENTS

| | | |
|---|---|---|
| 4,501,585 A | 2/1985 | Friedman |
| 5,096,092 A | 3/1992 | Devine |
| 5,104,008 A | 4/1992 | Crisci |
| 5,142,610 A | 4/1992 | Augustine |
| 5,249,706 A | 10/1993 | Szabo |
| 5,797,313 A | 8/1998 | Rothley |
| 6,056,157 A | 5/2000 | Gehl et al. |
| 6,273,307 B1 | 8/2001 | Gross et al. |
| 6,703,590 B1 | 3/2004 | Holley, Jr. |
| 6,766,106 B2 | 7/2004 | Roberson |
| 6,938,801 B1 | 9/2005 | Reddy et al. |
| 7,007,824 B2 | 3/2006 | Danby et al. |
| 7,021,206 B2 | 4/2006 | Eckenhausen et al. |
| 7,021,496 B2 | 4/2006 | Almond |
| 7,104,184 B2 | 9/2006 | Biderman |

(Continued)

*Primary Examiner* — Viren A Thakur
*Assistant Examiner* — Chaim A Smith
(74) *Attorney, Agent, or Firm* — Joe R. Prieto

(57) ABSTRACT

A free-standing, portable apparatus or appliance adapted for receiving a first container such as a pliable plastic bag containing a supply of a fluid such as breastmilk; the appliance adapted for storing, cooling, and/or heating the first container and the fluid contained in the first container; the appliance adapted for dispensing the supply of fluid from the first container; and the appliance adapted for dispensing warm fluid such as breastmilk from the first container into a second container such as a standard baby bottle for instant feeding of the fluid such as breastmilk to an infant; and a process for dispensing warm fluid such as breastmilk from the first container.

2 Claims, 24 Drawing Sheets

(56) References Cited

U.S. PATENT DOCUMENTS

| | | |
|---|---|---|
| 7,316,249 B2 | 1/2008 | Cheong |
| 7,475,795 B2 | 1/2009 | Faller et al. |
| 7,661,560 B2 | 2/2010 | Murray |
| D632,921 S | 2/2011 | Kang |
| 8,083,102 B2 | 12/2011 | Murray |
| 8,167,006 B1 | 5/2012 | Mathis et al. |
| 8,261,944 B2 | 9/2012 | Krause et al. |
| 8,360,279 B1 | 1/2013 | Giles |
| 8,701,906 B1 | 4/2014 | Anderson |
| 2008/0277417 A1 | 11/2008 | Groesbeck |
| 2009/0088684 A1 | 4/2009 | Rohrig |
| 2011/0209625 A1 | 9/2011 | Kang |
| 2012/0211521 A1 | 8/2012 | Moeggenberg et al. |
| 2014/0376894 A1 | 12/2014 | Bauer et al. |

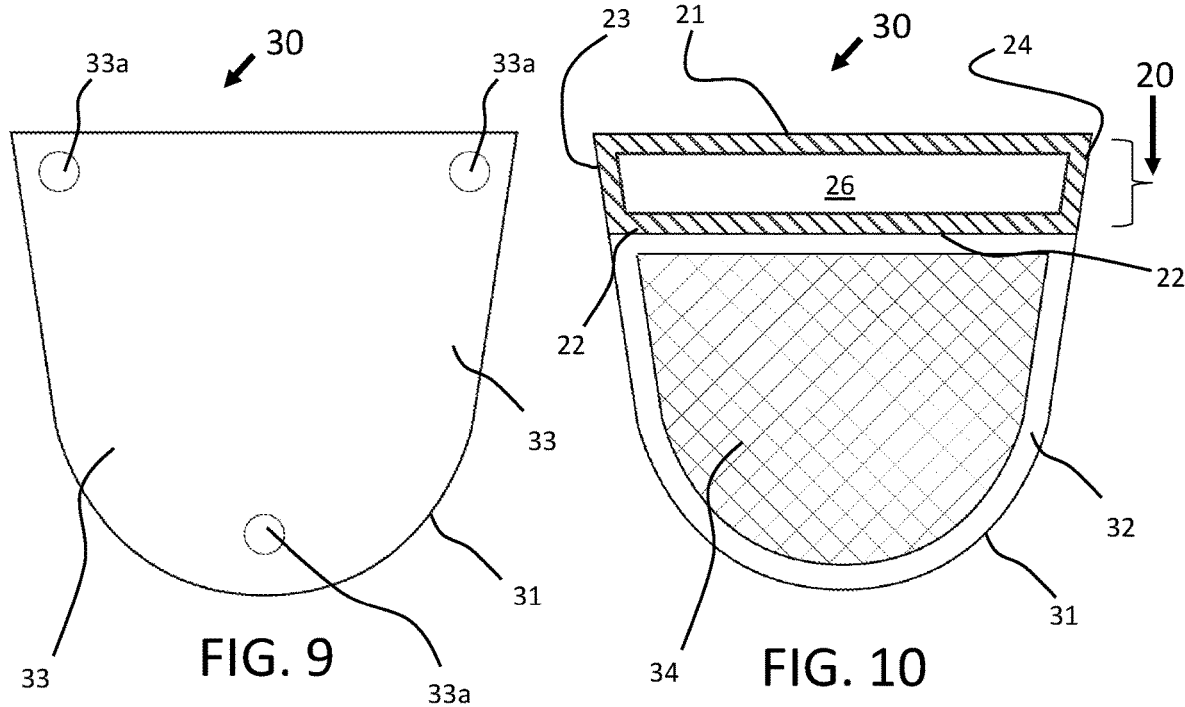
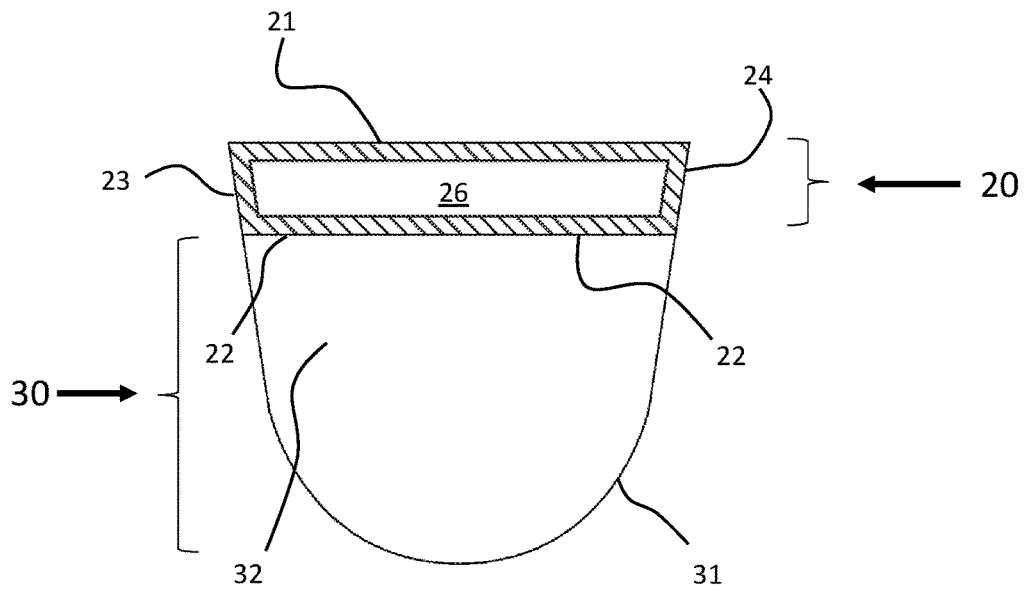

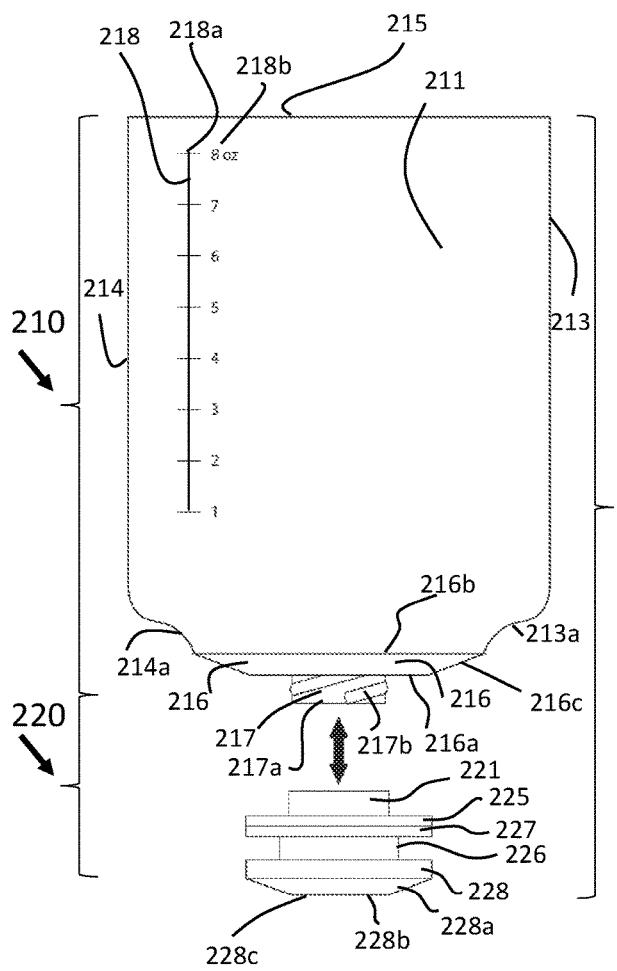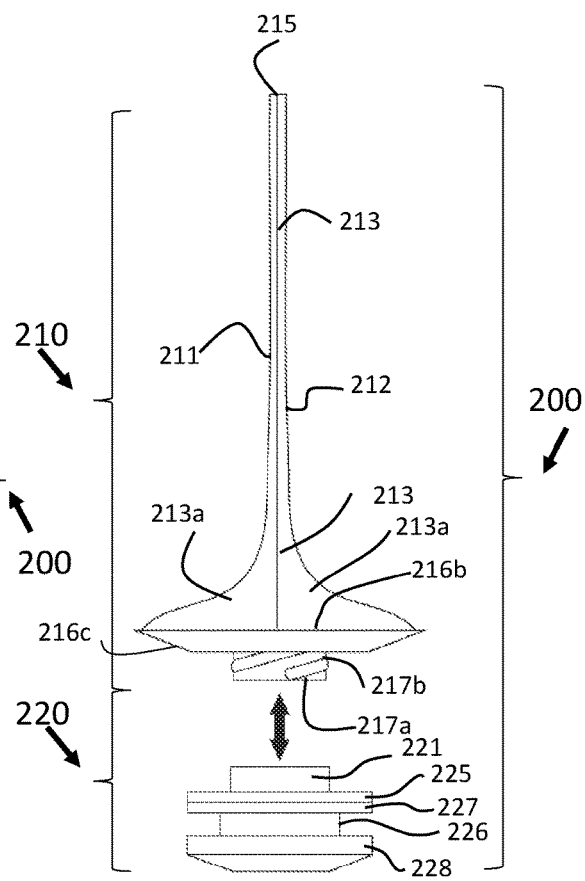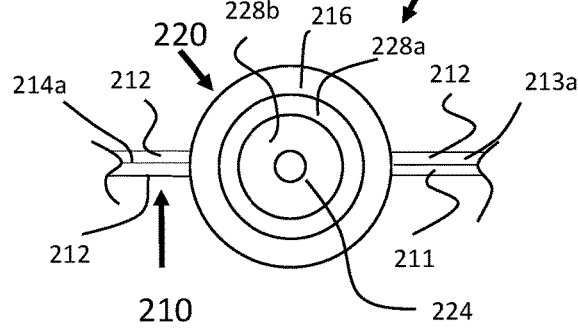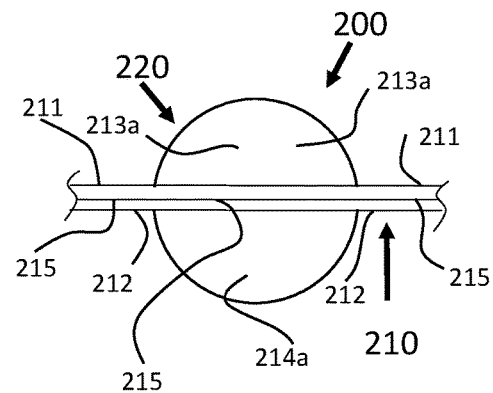
FIG. 16
FIG. 17
FIG. 18
FIG. 19

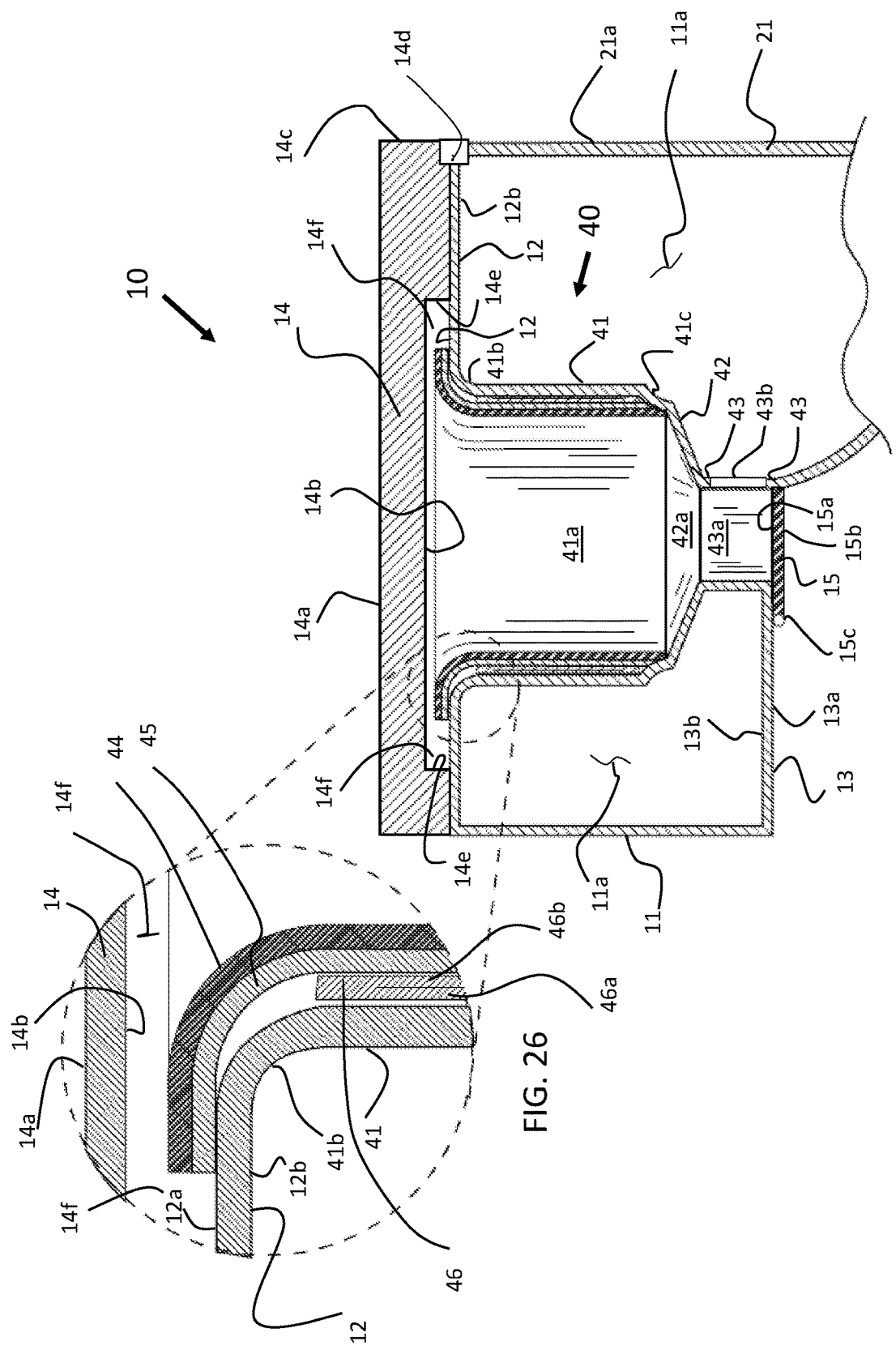

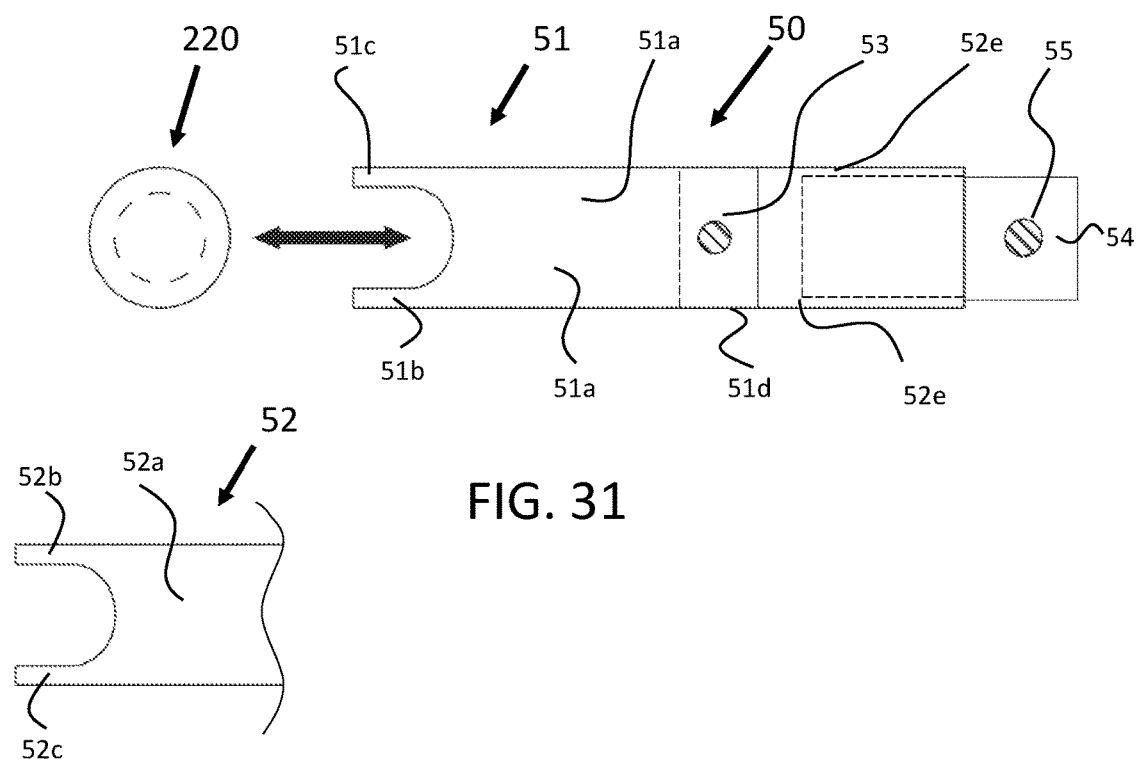
FIG. 31
FIG. 32
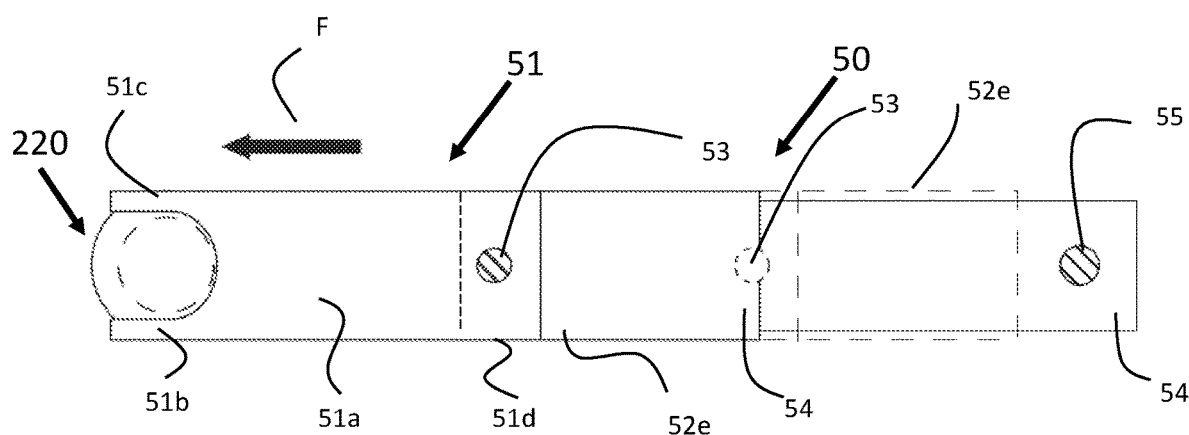
FIG. 33

FLUID DISPENSER

FIELD

The present invention relates to an apparatus and a method for preparing, storing, and dispensing a liquid fluid. In a more specific embodiment, the present invention relates to an apparatus and a method for preparing, storing, and dispensing breastmilk.

BACKGROUND

Various portable apparatuses for dispensing various fluids are known in the art. For example, known portable apparatuses include machines or appliances for dispensing fluids such as coffee, soda, tea, milk, infant formula, and other fluid beverages. For example, a commercially available appliance for dispensing hot coffee is one that is sold under the trademark Keurig® (trademark of Keurig Green Mountain, Inc.). Another example of a commercially available appliance includes an appliance for dispensing infant formula and sold under the trademark BabyNes® (trademark of Nestle).

While each of the known appliances share common features and components, each of the known appliances are uniquely designed for dispensing a particular fluid; and a particular dispensing machine for dispensing a specific fluid beverage may not function to dispense another different fluid or beverage. Therefore, such prior known dispensing machines or appliances cannot be used to dispense a different beverage other than for the beverage the dispensing machine was built to dispense.

In addition, a problem associated with prior dispensing devices is the threat of contamination of a fluid that must remain sanitized throughout the entire process of dispensing. For example, breastmilk is a fluid that should be kept free of contamination from the time the breastmilk is expressed from a mother's breast to the time the breastmilk is fed to a baby's mouth. However, contamination of breastmilk can occur from several sources. For example, breastmilk may become contaminated when the breastmilk contacts parts of devices used to handle the breastmilk such as a storage container, pumping device, or dispensing device. During dispensing or during handling of the breastmilk, the breastmilk can also become contaminated by baby caregiver responsible for handling the breastmilk by the caregiver physically touching the breastmilk. Breastmilk can also become contaminated during the transfer of breastmilk between multiple vessels (e.g., transfer of the breastmilk from a breastmilk pump bottle, to a storage container, and then ultimately to a baby bottle). Also, if the breastmilk is exposed to the air atmosphere, the breastmilk may become contaminated from airborne pollutants/contaminants. Accordingly, there is a real need in the industry for a device, machine, or apparatus and method for preparing, storing, and dispensing a fluid such as breastmilk in an expedient, efficient, convenient, economical, and sanitary manner; and with less human interaction.

In addition, for some fluids such as breastmilk, there are no known portable devices for dispensing a fluid efficiently and on-demand in a noninvasive and non-contaminating manner during dispensing of the fluid. It is therefore desired to provide a dispensing apparatus that overcomes the problems of the prior art dispensing devices by providing a dispenser including a closed chamber (to reduce the chance of airborne contamination/pollution); a cooling system for keeping the fluid, such as breastmilk, cooled during storage; a warming system to bring the fluid, such as breastmilk, to a serving temperature before dispensing; and a dispensing system for dispensing the fluid in a sanitary, noninvasive and non-contaminating manner.

SUMMARY

The present invention is generally directed to an apparatus and method for preparing and dispensing, in a non-contaminating manner, a fluid or liquid product in particular a comestible fluid dispensed for consumption. More specifically, the present invention is directed to a free-standing, portable apparatus and method for storing, preparing and dispensing a supply of a liquid product on-demand and in a sanitary manner. In one preferred embodiment, the liquid product to be dispensed using the portable apparatus can be, for example, breastmilk, a fluid that is to be fed to an infant on-demand.

In accordance with the present invention, one embodiment is directed to a portable apparatus adapted for storing, preparing and dispensing a supply of fluid in a non-invasive and non-contaminating manner; the apparatus including:

(a) a housing including a chamber portion having a top surface and bottom surface;

(b) a housing including a machine compartment portion;

(c) a support base portion having a top surface and a bottom surface;

wherein the machine compartment portion is integral to the chamber portion and the base portion; wherein the base portion is integral with the machine compartment portion forming a space in a vertical plane between the top surface of the support base portion and the bottom surface of the chamber portion;

(d) a receptacle vessel integrally disposed in said chamber portion; wherein said vessel is adapted for receiving a first container containing therein a predetermined volume of fluid;

(d1) a cooling means disposed in said compartment portion; wherein said cooling means is adapted for cooling the chamber portion to a preselected first temperature and maintaining the first container in the chamber portion at the first temperature for a period of time until the fluid is ready to be dispensed from the apparatus and used; and/or (d2) a heating means disposed in said compartment portion; wherein said heating means is adapted for heating the chamber portion to a preselected second temperature and warming, defrosting or thawing the fluid contained in the first container to the second temperature for a period of time until the fluid is ready to be dispensed from the apparatus and used; and (e) a means for transferring, in a noninvasive and non-contaminating manner, a preselected volume of fluid contained in the first container disposed in the receptacle vessel of said chamber portion, from said first container into a second container disposed on the top surface of the support base portion in the space between the top surface of the support base portion and the bottom surface of the chamber portion.

Another embodiment of the present invention is directed to a process of preparing breastmilk for feeding a baby on-demand by a caregiver including the steps of:

(a) providing a frozen or refrigerated bag containing frozen or refrigerated breastmilk;

(b) placing the frozen solid bag containing the frozen breastmilk into the above portable apparatus;

(c) warming the breastmilk in the flexible bag by heating the bag using a heating means in the above portable apparatus to a predetermined proper temperature that is safe for feeding a baby without burning or injuring the baby; and (d) dispensing a volume of fluid liquid of breastmilk from the flexible bag in the above portable apparatus into a baby bottle adapted for use in feeding a baby.

Still another embodiment of the present invention is directed to a method of dispensing a fluid, such as breastmilk, from a container including the steps of:

(a) providing a container removably connected to a valve; said valve having a reclosable opening therein; wherein the valve is in fluid communication with the contents of the container when the valve is in the open position; and (b) actuating the valve of the container into an open position such that the fluid in the container flows through the opening in the valve to allow the contents of the container to flow out of the container; wherein the valve is actuated with an actuating device in a non-invasive and non-contaminating manner, and without the actuating device contacting the fluid.

Yet another embodiment of the present invention includes a container article for use in a fluid-dispensing apparatus comprising a flexible bag removably connected to a push-pull valve; said push-pull valve having a reclosable opening therein in fluid communication with the contents of the container such that when the push-pull valve is in the open position the fluid in the flexible bag flows through the opening in the valve and the contents of the flexible bag flow out of the bag; wherein said push-pull valve is adapted for being opened in a non-invasive and non-contaminating manner.

Even still another embodiment of the present invention includes a process of preparing breastmilk for feeding a baby on-demand by a caregiver including the steps of:

(a) providing a frozen or refrigerated bag containing frozen or refrigerated breastmilk;

(b) placing the frozen or refrigerated bag containing the frozen or refrigerated breastmilk into the above portable apparatus;

(c) warming the breastmilk in the flexible bag to form a fluid liquid of breastmilk by heating the flexible bag using a heating means located in the above portable apparatus to a predetermined proper temperature that is safe for feeding a baby without burning or injuring the baby; and (d) dispensing a volume of the fluid liquid of breastmilk from the flexible bag located in the above portable apparatus into a baby bottle located outside and adjacent the above portable apparatus, wherein the baby bottle is adapted for use in feeding a baby.

In accordance with still another preferred embodiment, the present invention includes a free-standing, portable appliance adapted for storing, preparing and dispensing a supply of fluid such as breastmilk for on-demand feeding to an infant; wherein the appliance comprises:

(a) a housing integral with a support base portion;

(b) a chamber supported in said housing, said chamber adapted for receiving a container containing therein a predetermined volume of frozen or refrigerated breastmilk at a first frozen or refrigerated temperature;

(c) a warming means disposed in said chamber for warming and defrosting said frozen or refrigerated breastmilk contained in the container to a preselected second temperature such that the frozen or refrigerated breastmilk transforms into a volume of flowable liquid breastmilk contained in said container; and (d) a transfer means disposed in said chamber adapted for transferring said volume of flowable, fluid liquid breastmilk from the container into a baby bottle.

In accordance with the above preferred embodiment, the appliance of the present invention is adapted for: (1) receiving a frozen or refrigerated bag containing a supply of breastmilk in a cold state; (2) storing the bag in its cold state by a refrigerating means in the appliance for a period of time until the breastmilk in the bag is needed for feeding an infant; (3) warming the frozen or refrigerated bag to form a warm pliable bag while concurrently warming the breastmilk in the bag to form a fluid flowing breastmilk and warming the breastmilk to a proper temperature for feeding the warmed breastmilk to an infant; and (4) transferring the warm breastmilk from the resulting warm pliable bag into a standard baby bottle for quickly feeding of the breastmilk to an infant.

Other embodiments of the appliance of the present invention which can be ascertainable by the skilled artisan include, for example, controls for ensuring that the breastmilk in the bag does not exceed or overshoot a maximum safe temperature for feeding the breastmilk to an infant. The appliance may also include a visual indicator that indicates the temperature of the breastmilk is in a safe temperature range to reassure the caregiver of a proper temperature.

Another preferred embodiment of the present invention includes a method of feeding breastmilk to a baby on demand, i.e., in real time when a baby caregiver is ready to feed a baby, the process including the steps of:

(a) providing a frozen or refrigerated bag containing frozen or refrigerated breastmilk;

(b) providing a free-standing, portable apparatus/appliance adapted for storing, preparing and dispensing a supply of breastmilk for on-demand feeding to an infant;

(c) placing the frozen or refrigerated bag containing the frozen or refrigerated breastmilk into the above apparatus of step (b);

(d) warming the breastmilk contained in the flexible bag to form a flowable liquid breastmilk in the flexible bag by heating the bag, using a heating means disposed in the apparatus, to a predetermined proper temperature that forms a flowable liquid breastmilk and that is safe for feeding a baby without burning or injuring the baby; and (e) dispensing a volume of the flowable liquid breastmilk from the flexible bag in the apparatus into a baby bottle adapted for use in feeding a baby; said dispensing step carried out without the flowable liquid breastmilk contacting surfaces of the apparatus or its elements.

The above process can be preferably employed at a later time after the following prior steps have been taken:

(a) attaching a breast pump device to a mother's breast;

(b) pumping a volume of breastmilk directly from the mother's breast to a flexible bag using the breast pump; and (c) freezing or refrigerating the flexible bag containing the breastmilk for later use.

Yet another embodiment of the present invention is directed to a container for holding a liquid comestible and for dispensing the liquid comestible therefrom; and more particularly, to a valved container having an actuating valve adapted for dispensing a liquid comestible such as milk, fruit juice, or the like from the container in a sanitary manner.

One object of the present invention is to provide an apparatus and method for preparing, storing, and dispensing liquid fluid in an expedient, efficient, convenient, economical, and hygienic or sanitary manner with less human interaction and contact. In particular, it is an object of the present invention to provide an apparatus that is able to dispense a liquid fluid such as breastmilk in an efficient and hygienic manner.

BRIEF DESCRIPTION OF THE DRAWINGS

The present invention, together with further objects and advantages thereof, may best be understood by reference to the following drawings. The drawings provided herein illustrate the primary parts of the present invention and how each part has been arranged using illustrations to better understand the principles applied herein while not involving specific methods of connection between the primary components described. In addition, the embodiments illustrated by the drawings and described herein are not necessarily preferred choices of the process, apparatus, or material composition of the described embodiments, which might otherwise limit the present invention from being constructed with alternate materials for other uses. Instead, the embodiments of the present invention shown in the drawings are provided herein by way of example only; and the novel features of the present invention are set forth with particularity in the appended claims. In the several figures which follow, like reference numerals identify like elements, and:

FIG. 9 is a bottom elevation view of the apparatus of the present invention shown in FIG. 1.

FIG. 10 is a top elevation view, partly in cross-section, taken along line 10-10 of FIG. 2, showing one embodiment of the top surface of the base portion of the apparatus of the present invention.

FIG. 11 is a top elevation view, partly in cross-section, showing another embodiment of the top surface of the base portion of the apparatus of the present invention.

FIG. 16 is an exploded front elevation view of a flexible bag and a push-pull valve useful for the apparatus of the present invention and showing the front wall of the bag with no fluid in the bag.

FIG. 17 is an exploded side elevation view of the flexible bag and push-pull valve of FIG. 16.

FIG. 18 is a top elevation view of the flexible bag and push-pull valve of FIG. 16.

FIG. 19 is a bottom elevation view of the flexible bag and push-pull valve of FIG. 16.

FIG. 25 is a side cross-sectional view, partly broken away, of the chamber portion of the apparatus of the present invention taken along line 25-25 of FIG. 2.

FIG. 26 is a magnified side cross-sectional view of a portion of the chamber portion and receptacle vessel of the apparatus of the present invention of FIG. 25 and indicated by the área in dotted line.

FIG. 31 is a top elevation view of the valve actuation mechanism of FIG. 28 before the mechanism is actuated.

FIG. 32 is a bottom elevation view, partly broken away, of the valve actuation mechanism of FIG. 28 before the mechanism is actuated.

FIG. 33 is a top elevation view of the valve actuation mechanism of FIG. 28 after the valve actuation mechanism is actuated and engaged with the push-pull valve of the present invention.

DETAILED DESCRIPTION

Figure 1:
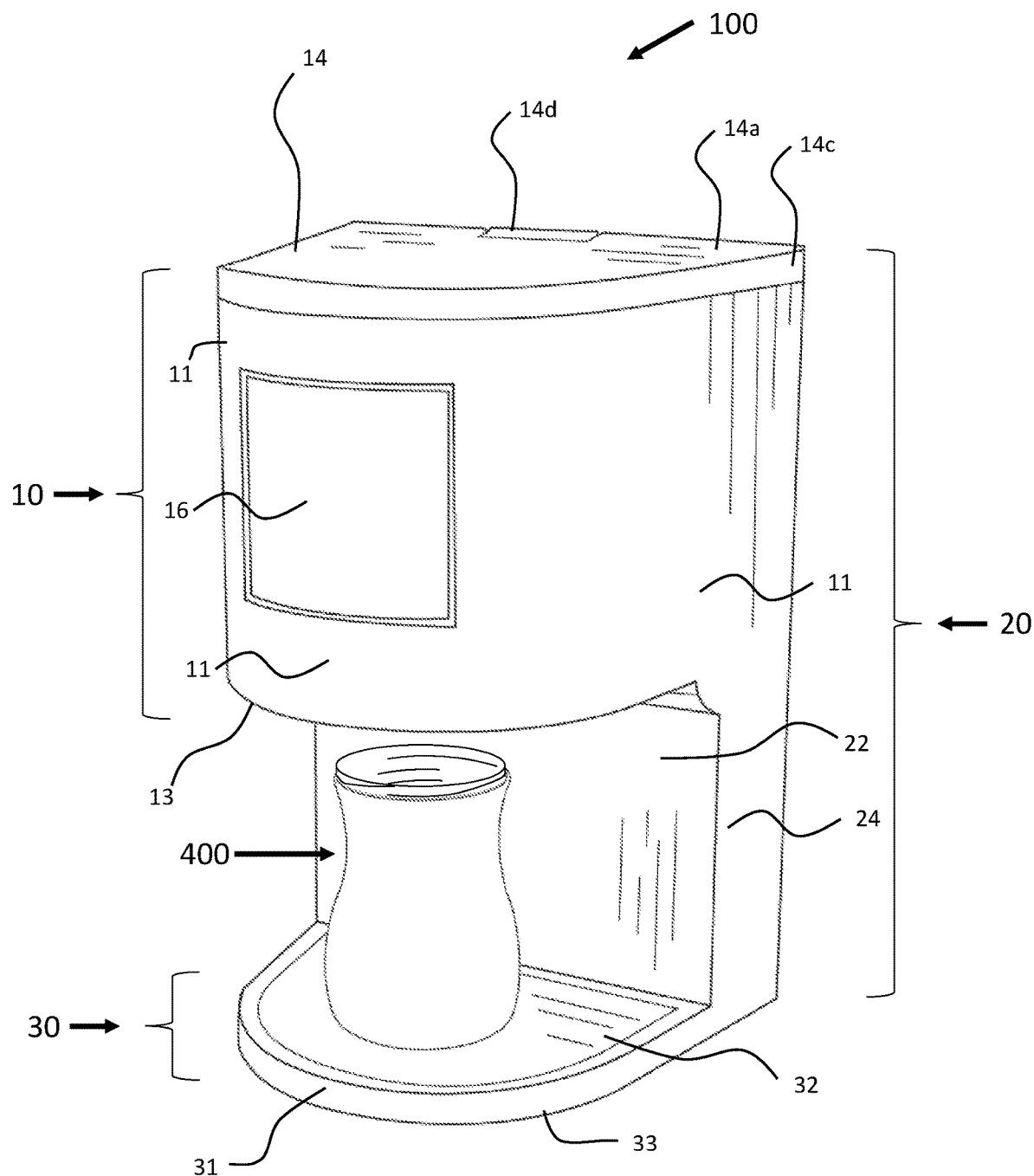
FIG. 1 is a perspective view of an apparatus of the present invention.

The terms "liquid", "fluid", "liquid fluid", "liquid product", or "liquid fluid product" are used interchangeably herein and refer to a product in a liquid or flowable form capable of being dispensed by the dispensing apparatus of the present invention in a sanitary manner, and includes for example, but not limited to, milk, breastmilk, baby formula, juices, iced tea, water, fruit drinks, lemonade, wine, coffee, chocolate, and other liquid beverages.

At the outset, the apparatus and method of the present invention will herein-after be described in conjunction with their use in the dispensing of breastmilk, but it will readily be appreciated by those skilled in the art that the description herein is only illustrative; and that the apparatus and method may be employed equally well in conjunction with the dispensing of substantially any other liquid product desired to be dispensed in a sanitary manner.

In the following detailed description, reference is made to the accompanying drawings, which form a part hereof, and in which is shown, by way of illustration, specific embodiments in which the present invention may be practiced. In the drawings, like numerals describe like components throughout the several views. These embodiments are described in sufficient detail to enable those skilled in the art to practice the present invention. Other embodiments may be utilized and structural, mechanical, or logical changes may be made to the embodiments described herein without departing from the spirit and scope of the present invention.

As aforementioned, the present invention relates to a method and means for hygienically handling and dispensing a liquid, particularly a liquid comestible product that has to be maintained free of contamination up to the time such liquid product is used and consumed. For example, a liquid breastmilk product, for consumption by an infant, should be unadulterated when fed to the infant. The apparatus and method of the present invention is adapted for dispensing a liquid product from a first storage container to a second feed container through the dispensing apparatus. The first storage container is generally a flexible bag adapted for holding and storing a liquid product for a predetermined period of time until the liquid product is ready for consumption. The second container is generally a ridge vessel (e.g. a baby bottle made of plastic or glass) adapted for feeding or delivering the liquid product to a human (e.g. an infant) for consumption.

The present invention has for one of its principal objects the provision of a method, and a means for carrying out the method, whereby the liquid product (e.g., breastmilk) can be handled from the liquid product's place of origin (e.g., a mother's breast) to the liquid product's place of disposition (e.g., an infant's mouth for feeding an infant) without the liquid product directly contacting surfaces of any dispensing equipment or human (e.g., a mother or caregiver) handling the dispensing equipment, so as to prevent equipment or human contamination.

With reference to FIGS. 1-45, there is shown one broad embodiment of the present invention dispensing apparatus generally indicated by numeral 100. The dispensing apparatus 100 is useful for dispensing a liquid fluid product, particularly a liquid fluid product such as breastmilk. The apparatus 100 is herein interchangeably referred to as a "dispenser", "fluid dispenser", or "breastmilk dispenser" 100.

Some of the elements of the breastmilk dispenser 100, as shown by the dispenser's outer features in FIGS. 1-11, include a combination of at least: (a) a housing forming a chamber portion generally indicated by numeral 10; (b) a housing forming a machine room or machine compartment portion generally indicated by numeral 20; and (c) a base member portion generally indicated by numeral 30. The elements 10, 20 and 30 are integrally connected to each other to form the apparatus 100 as herein described below in more detail. The apparatus 110 can be any shape. In FIGS. 1-11, the components 10, 20, and 30 together form a generally C-shaped dispenser when viewed in a side view; that is, the chamber portion, the machine compartment portion; and the support base portion are integral with each other that the combination forms a generally C-shaped configuration when viewed on one side of the apparatus.

Inside the chamber portion 10 of the dispenser 100 is a receptacle vessel generally indicated by numeral 40 (described in more detail herein below with reference to FIGS.

25-27); the vessel 40 being generally conterminous with the chamber portion 10. Also, enclosed within the chamber portion 10 of the dispenser 100 is an actuation mechanism generally indicated by numeral 50 (described in more detail herein below with reference to FIGS. 28-33 and FIGS. 41-45). Inside the interior space of the compartment portion 20 of the dispenser 100 are various mechanical, electrical, and pneumatic unit operations with functioning elements of the apparatus to assist in operating the dispenser 100, including for example, a cooling mechanism generally indicated by numeral 60, a heating mechanism generally indicated by numeral 70, a pneumatic mechanism generally indicated by numeral 80, and electrical components generally indicated by numeral 90 (shown in FIG. 12 and described in more detail herein below).

Figure 12:
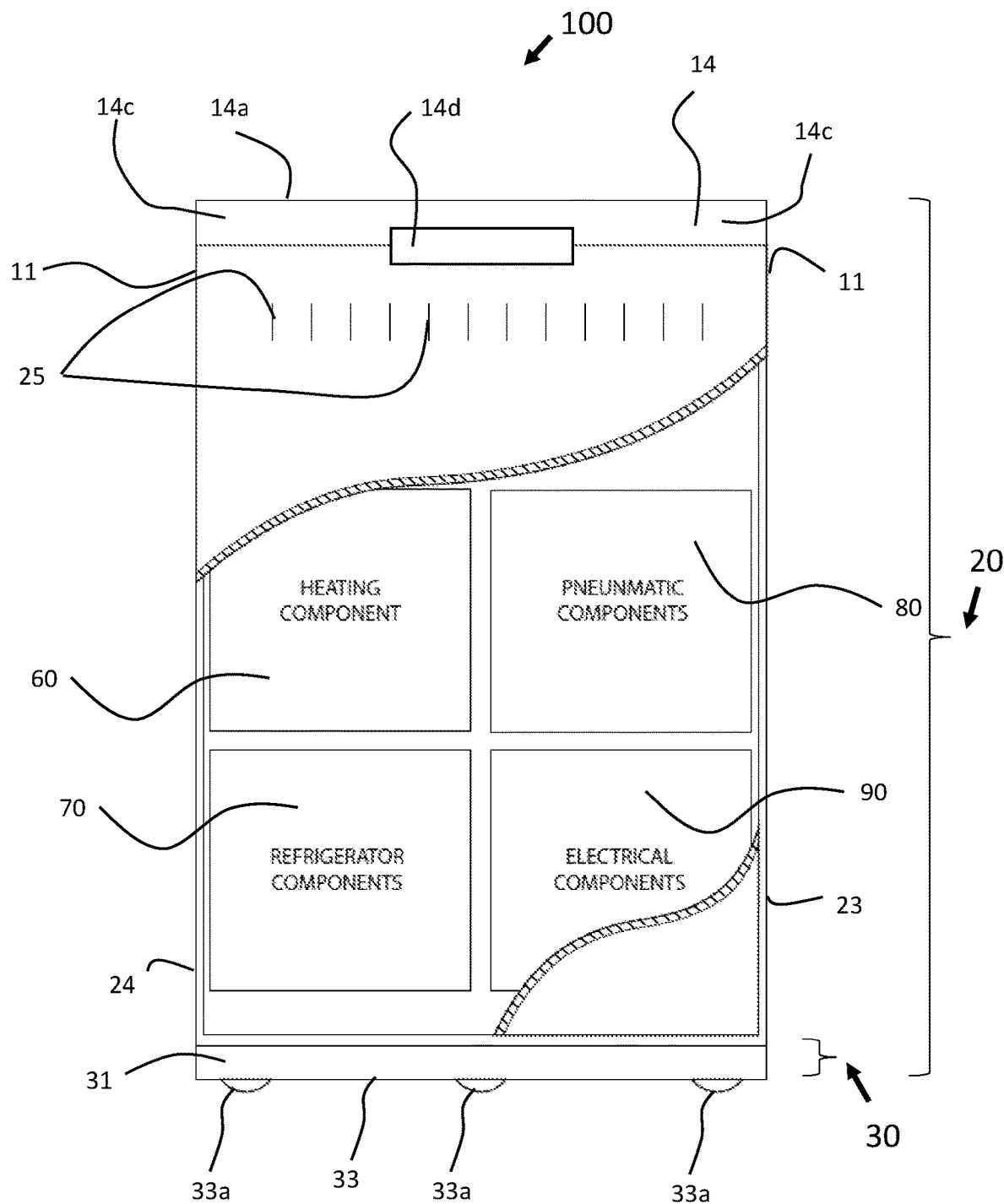
FIG. 12 is a back elevation view, partly in cross-section and partly broken away, of the machine compartment portion of the apparatus of the present invention generally showing various components contained therein.
Figure 13:
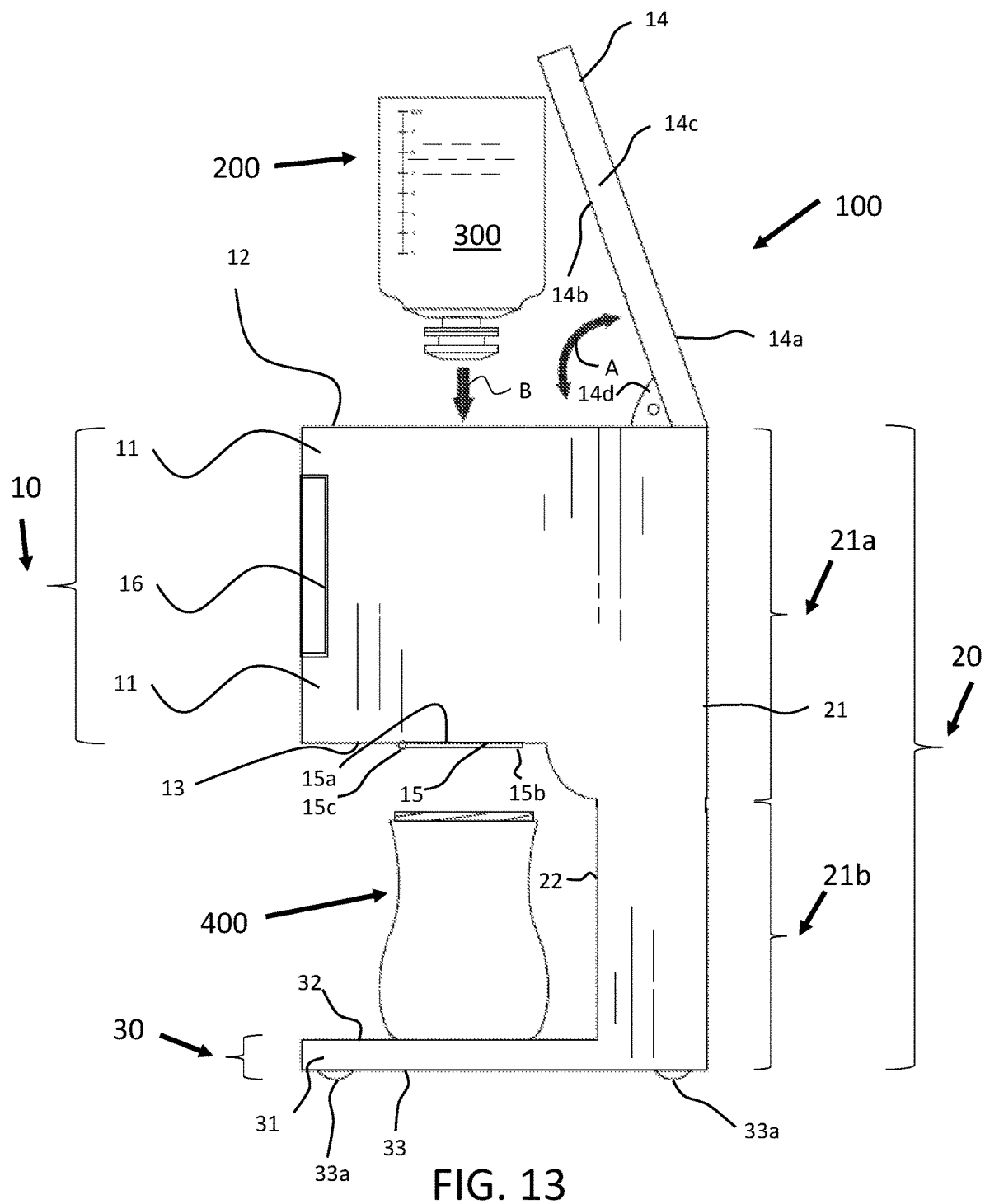
FIG. 13 is a side elevation view of the apparatus of the present invention showing an open lid of the chamber portion of the apparatus of the present invention receiving a first container.
Figure 14:
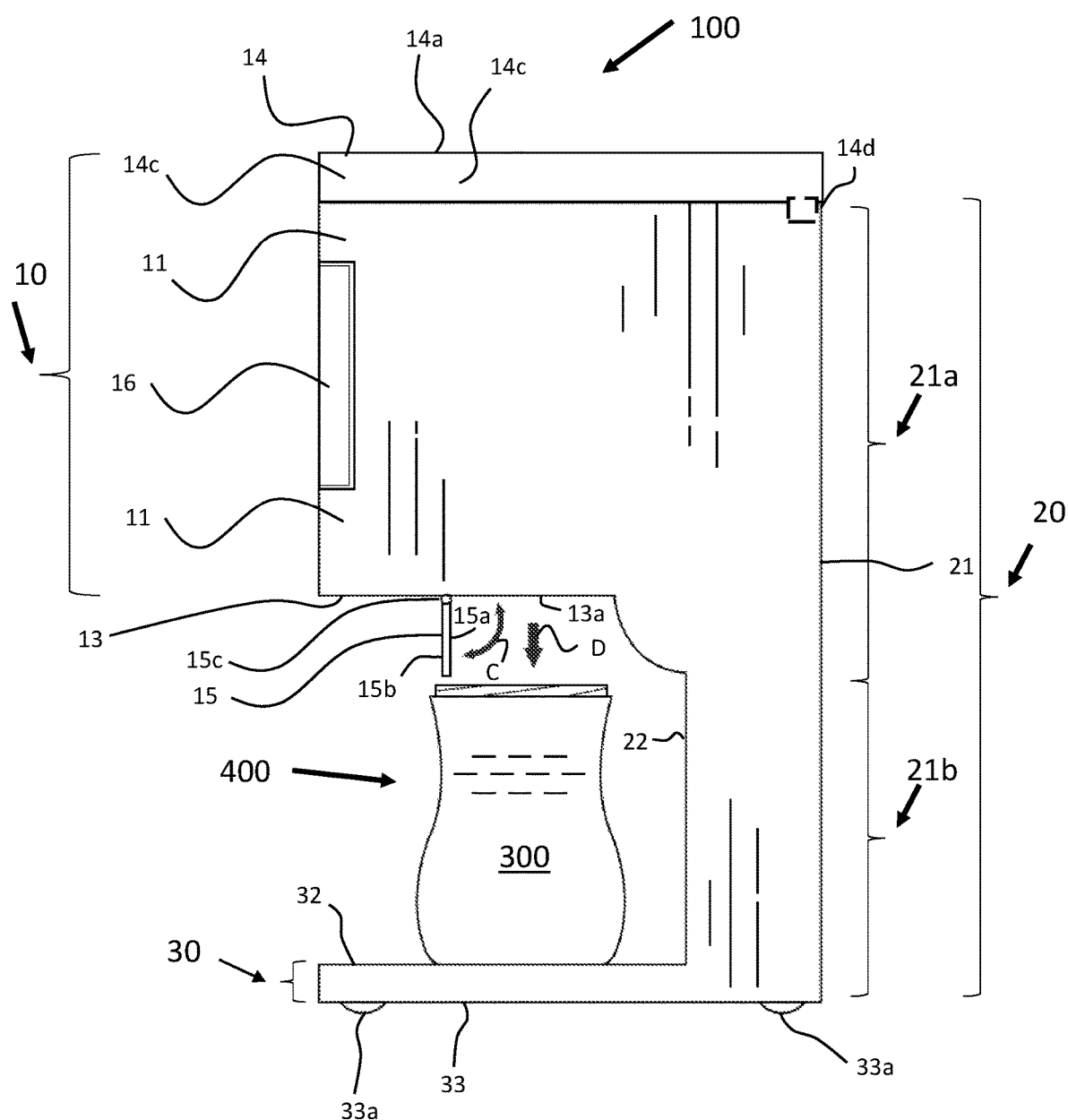
FIG. 14 is a side elevation view of the apparatus of the present invention showing a closed lid of the chamber portion of the apparatus of the present invention after the chamber portion has received the first container, and a bottom door of the chamber portion open.
Figure 15:
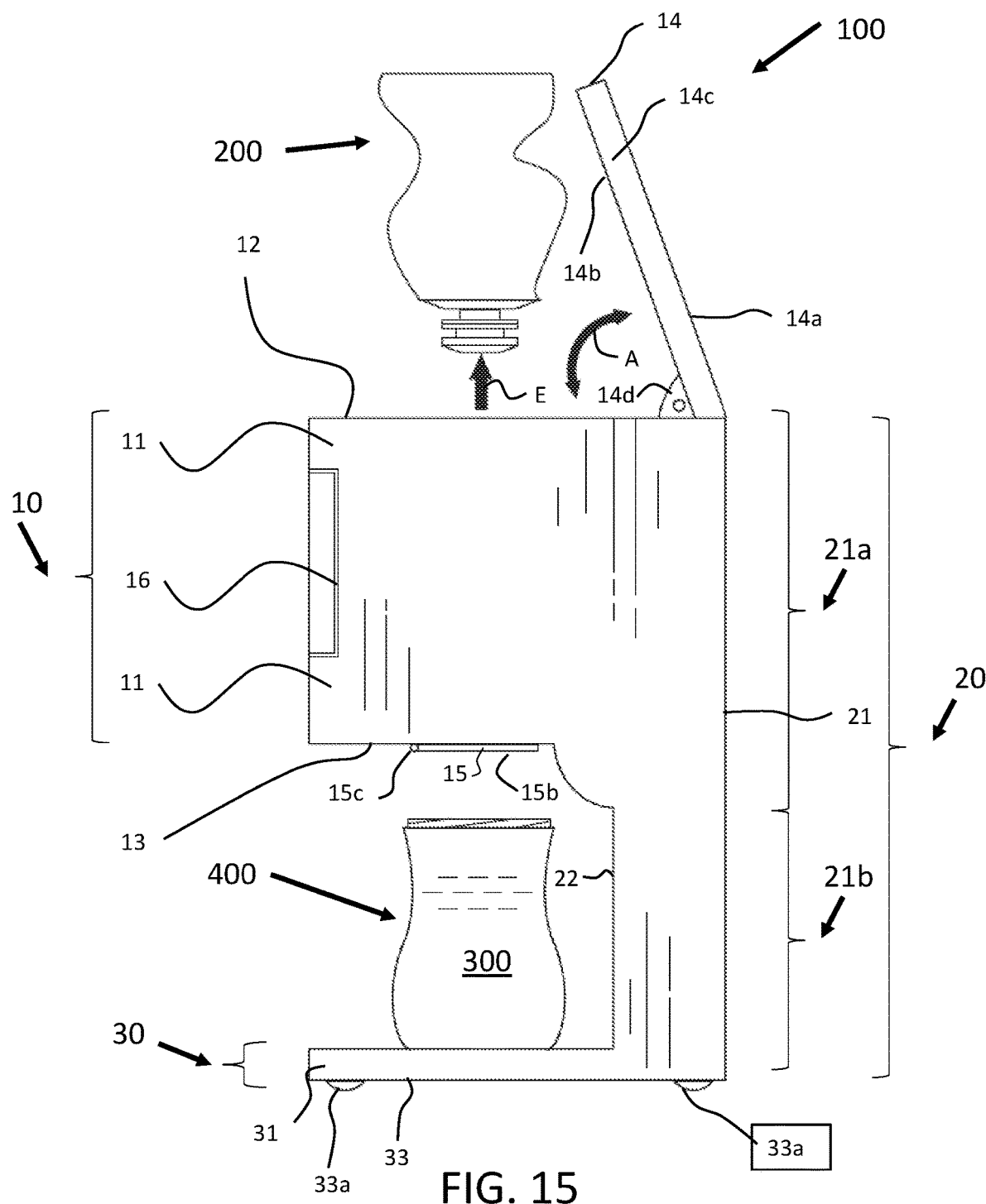
FIG. 15 is a side elevation view of the apparatus of the present invention showing an open lid of the chamber portion of the apparatus of the present invention and an empty first container being removed from the chamber portion.
Figure 20:
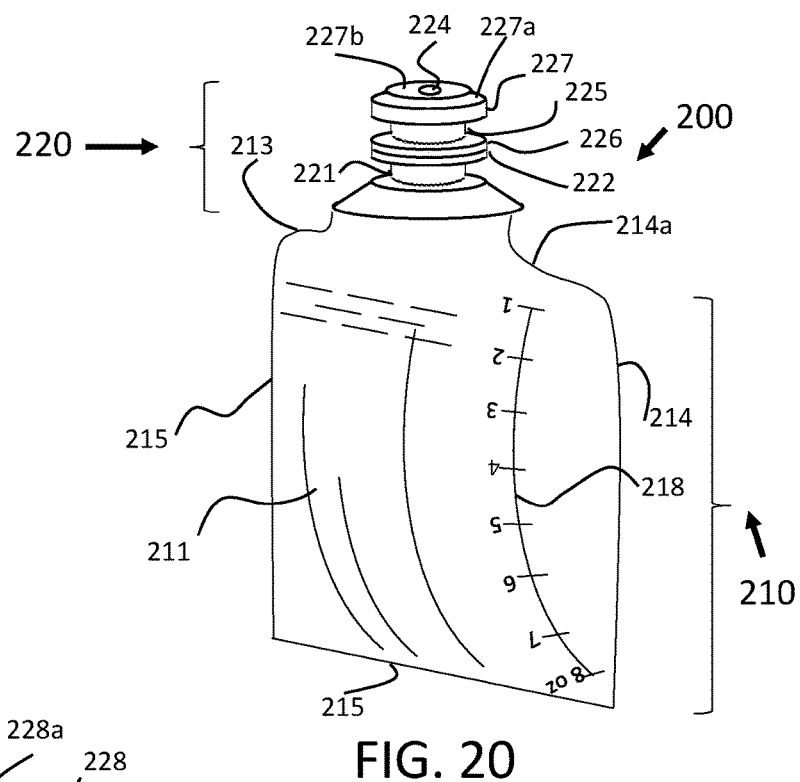
FIG. 20 is a perspective view of a flexible bag coupled with a push-pull valve; the bag containing fluid therein.
Figures 21, 22:
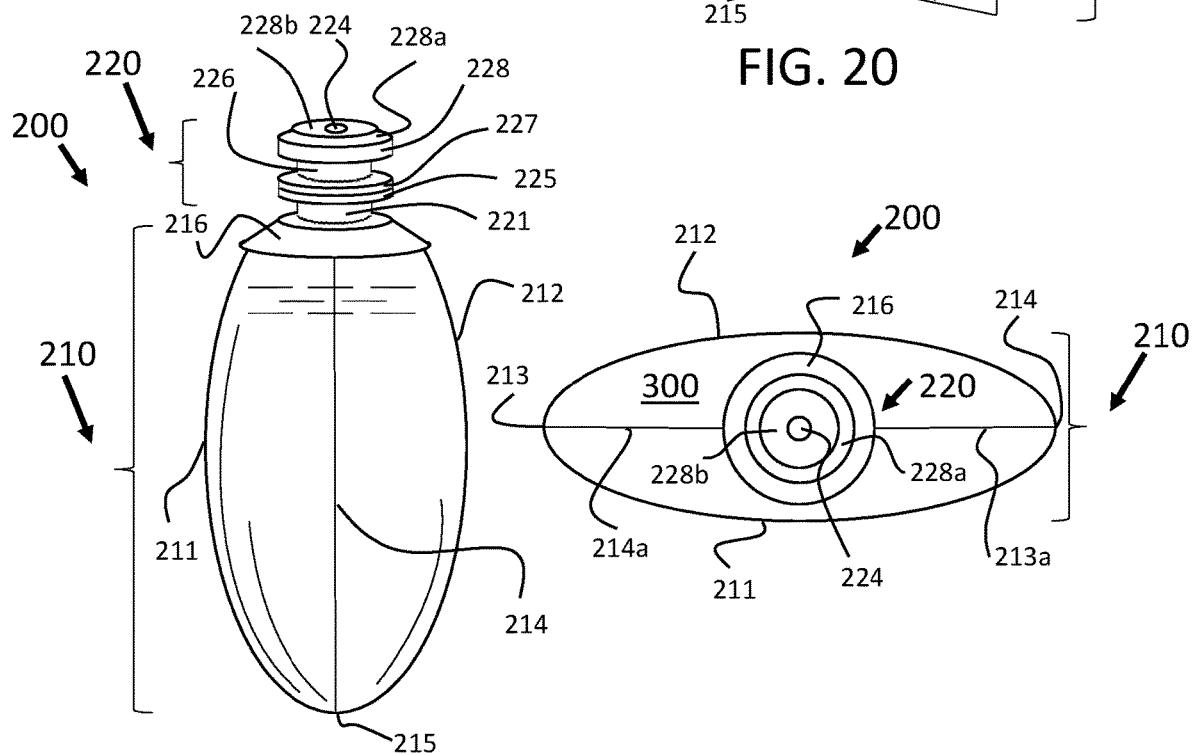
FIG. 21 is a side elevation view of the flexible bag and push-pull valve of FIG. 20.
FIG. 22 is a top elevation view of the flexible bag and push-pull valve of FIG. 20.

With reference to FIGS. 1-15, and more particularly with reference to FIGS. 13-15, there is shown a general procedure for operating the fluid dispenser 100. The dispenser 100 is adapted for receiving a re-sealable flexible first container generally indicated by numeral 200 (for example, a flexible film bag container 200 shown in FIG. 13 and FIGS. 16-22); the first container being closed initially. The first container 200 is adapted for containing a liquid product generally indicated by numeral 300 (for example, breastmilk 300 shown in FIG. 13). As shown in FIG. 13, a lid 14 of the dispenser can be opened (in the direction as indicated by arrow A) and a breastmilk bag 200 may be inserted (in the direction as indicated by arrow B) into the chamber portion 10 of the dispenser. When the bag 200 is inside the chamber portion 10, the lid 14 can be closed (in the direction as indicated by arrow A), and the bottom door 15 of the chamber portion 10 can be opened (in the direction as indicated by arrow C), as shown in FIG. 14. The actuation mechanism 50 (not shown in FIG. 14) located inside the chamber portion 10 opens the bag 200 inside the chamber portion 10 and fluid 300 inside the interior of the bag 200 is dispensed from the bag 200 through the chamber portion 10 (in the direction as indicated by arrow D) into a second container generally indicated by numeral 400 disposed on top of the base portion 30. Once dispensing is complete, the lid 14 of the chamber portion 10 can be opened (in the direction as indicated by arrow A) and the empty bag 200 can be removed (in the direction as indicated by arrow E) from the chamber portion 10 of the dispenser 100 as shown in FIG. 15.

First Container

The first container 200 may comprise, for example, any fluid impermeable (liquid-tight) pliable plastic container for holding a liquid product such as liquid infant breastmilk 200. Other containers embodying the bag 200 that are compatible with the breastmilk dispenser 100 of the present invention may include, for example, any known flexible, pliable, flaccid liquid-impermeable bag, pouch or liner that can: (1) be filled with and hold a liquid fluid such as breastmilk; (2) be sealed for storage in a liquid-tight manner; (3) undergo storage temperatures, for example, in a refrigerated environment (e.g., a refrigerator, freezer, cooler or the like); and (4) undergo heated temperatures for thawing out a cooled or frozen liquid contained inside the bag 200. In one embodiment, the bag 200 may be at least partially collapsible; and the bag 200 may be at least partially expandable. Once the bag 200 is filled with a fluid such as breastmilk and sealed, the bag 200 may then be placed in the refrigerated environment so that the breastmilk may be stored and preserved for future use.

The bag 200 may be selected from any number of standard flexible bags known in the art. For example, the first container 200, adapted to being filled with breastmilk, may include various known containers such as a disposable, sterile bag described in U.S. Pat. No. 6,328,082; a disposable, liquid-impermeable sterile plastic liner described in U.S. Pat. No. 6,050,432; and a bag described in U.S. Patent Application Publication No. US20140107608 A1, all of which are incorporated herein by reference.

With reference to FIGS. 16-22, there is shown one preferred embodiment of a unique and non-standard first container 200 particularly useful with the apparatus of the present invention which includes for example a flexible re-sealable film plastic liner, pouch or bag 200 having a bag body generally indicated by numeral 210 removably attached to a valve/opening member generally indicated by numeral 220. The bag 200 is adapted for being filled with breastmilk and adapted for holding the breastmilk 300 in the internal space (interior compartment) of the bag 200. The breastmilk bag 200 containing breastmilk 300 therein is of a size adapted for being placed in the receptacle vessel 40 of the chamber portion 10 of the breastmilk dispenser 100 for cooling or heating the bag 200 and its contents (as described herein below with reference to FIGS. 34-40).

In accordance with the present invention, as shown in FIG. 16-22, the breastmilk bag 200 containing breastmilk 300 can be closed to form a liquid-tight container. In FIGS. 16 and 17, the breastmilk bag 200 is shown without containing fluid. Also, the bag 200 is shown in an inverted vertical position because when the bag 200 is in use, the bag 200 is typically placed in the receptacle vessel 40 of the chamber portion 10 of the apparatus 100 in generally an inverted position with the valve/opening 220 of the bag 200 faced in a downward vertical plane direction such that the fluid (e.g., breastmilk) in the bag can flow in a downward vertical direction, for example, by gravitational force once the valve of the bag 200 is actuated into the open position. The closed bag 200 containing fluid 300 therein, is adapted to being received by the receptacle vessel 40 located in the dispenser chamber portion 10, in an inverted vertical plane direction (i.e., upside down) position, which is typically the preferred direction for placing the bag 200 inside the dispenser 100.

In one preferred embodiment, the breastmilk bag 200 includes, for example, a bag body 210 and a removable valve member 220 of a "push-pull valve" type (e.g., similar to the valves used with disposable water bottles). The push-pull valve when coupled to the bag body 210 can provide linear flow motion of the breastmilk 300 from the bag 200, in the receptacle vessel 40 of the chamber portion 10, to the second container 400. Optionally, a cap or cover member (not shown) may be used to fit over and cover the push-pull valve 220 when the bag is being stored or is not in use.

Bag Body

With reference to FIGS. 16-22 again, there is shown the bag body 210 including a generally cylindrical housing and when formed into the bag body 210, for example by heat sealing two sheets of flexible plastic material to form the housing the bag body 210. The bag body 210 may comprise a front wall 211 and a back wall 212 with side edges 213 and 214, with tapered top portions 213a and 214a, respectively; and a bottom edge 215. The bag body 210 may include a tapered cylindrical flange 216 integrally attached to the top portion of the bag body 210 comprising the walls 211, 212 and side edges 213, 214 (e.g., attached by heat sealing). The flange member 216 may include a top surface 216a and a bottom surface 216b with the bottom surface 216b of the flange 216 being integrally attached to the top portion of the bag body 210. The flange 216 may also include a tapered (angled) side wall 216c. The walls 211, 212 of the bag body 210 can be sealed together to form the sealed side edges 213, 214 and the sealed bottom edge 215. The flange 216 includes a tubular neck portion 217 integral to the top surface 216a of flange 216. The tubular neck portion 217 includes an orifice or opening 217a for receiving fluid into the interior space of the bag body 210; and for evacuating fluid from inside space of the bag body 210. Preferably, the neck 217 includes male threads 217b integral with the tubular neck portion 217. The neck threads 217b are adapted for threadedly receiving the push-pull valve member 220.

At least one of the front and rear side walls 211, 212 of the bag body 210 is provided thereon with indicia 218, for instance by printing, which indicates the approximate volume of liquid 300 (e.g. breastmilk) in the bag body 210. The indicia 218 may include for example, calibrated reference markings 218a to indicate liquid levels whereas the scale of volumes 218b, in ounces, is associated with each reference marking 218a such that the user can easily determine approximately the volume of liquid being dispensed, or having been previously dispensed or presently remaining in the bag body 210. Opposite each scale of volume indicia 218b, there is provided an indication of the volume measurement unit 218c (i.e. "OZ" for ounces) associated with the scale of volumes 218b.

In a preferred embodiment, the breastmilk bag 200 used in the present invention includes the neck portion 217 with opening 217a and neck threads 217b which can either be: (i) fitted with a coupling member/adaptor (not shown) adapted for attaching the breastmilk bag 200 to a breast pump (not shown); or (ii) attached directly to a breast pump to allow the breast pump to pump breastmilk 300 directly from the breast into the breastmilk bag 200; and thereby harvesting the breastmilk 300 for later use.

Typically, an intermediary container is used in a conventional process for harvesting breastmilk. By pumping directly from a breast into the breastmilk bag 200 using a breast pump, the sanitation of the breastmilk can be more easily maintained, and the time and cost of using the present invention can be reduced by removing the intermediary container. The coupling member/adaptor, when used, can be connected to the threads 217b on the neck 217 of the bag body 210 on one end of the adaptor and connected to any number of known breastmilk pump models on the other end of the adaptor. After the breastmilk 300 is pumped into the bag body 210 through the coupling/adapter, the coupling/adaptor and breast pump can be removed; and a push-pull valve 220 can be screwed onto the threads 217b of the neck portion 217 to close the opening 217a of the breastmilk bag body 210 such that the breastmilk 200 can be sealed liquid-tight.

Valve

The valve member 220 useful in the present invention, and its manner of operation for opening and closing, can generally be any known standard valve of the "push-pull" type such as for example a valve of the type described in U.S. Pat. No. 5,104,008A and European Patent No. EP0914280B1.

Figure 23:
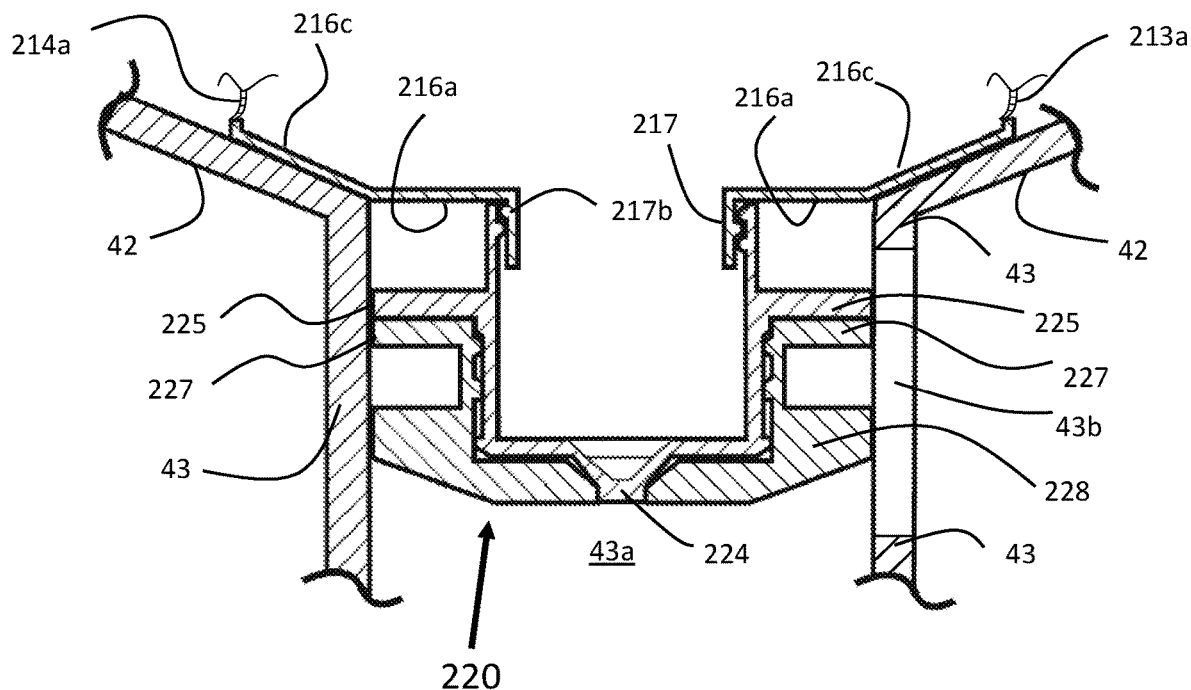
FIG. 23 is a magnified side elevation view, partly in cross-section and partly broken away, of a bottom portion of the chamber portion of the apparatus of the present invention showing a push-pull valve in a closed position.
Figure 24:
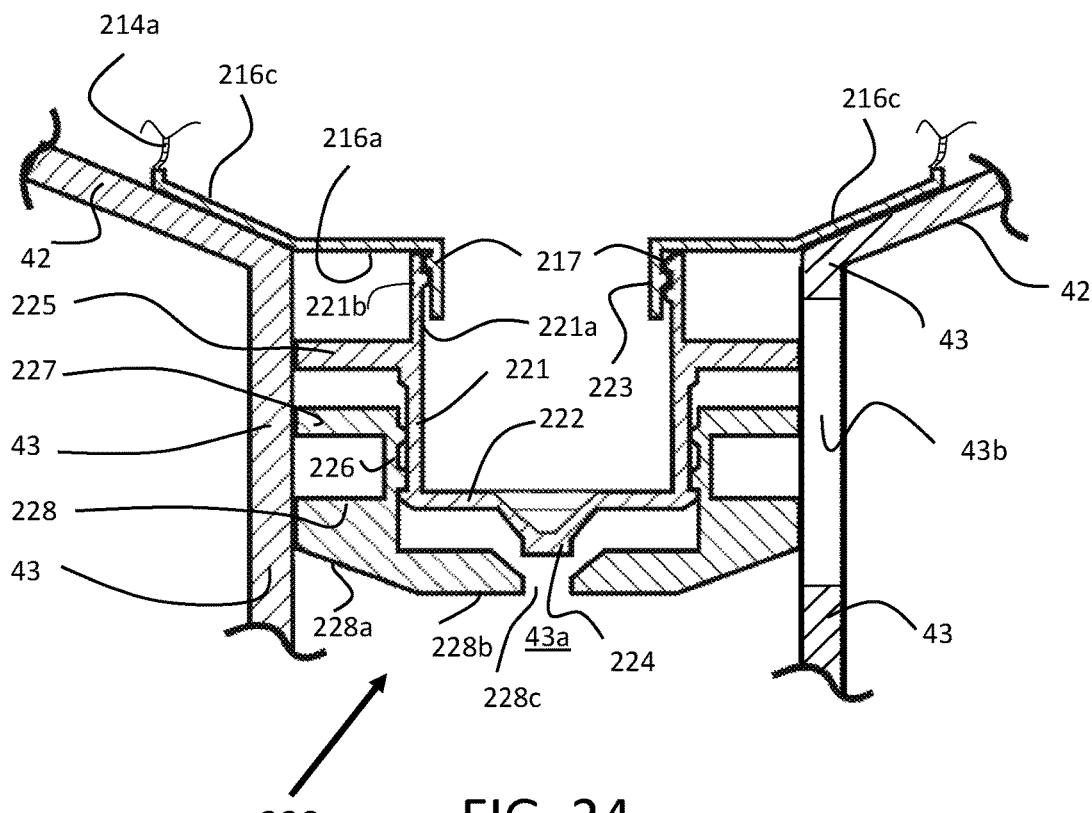
FIG. 24 is a magnified side elevation view, partly in cross-section and partly broken away, of a bottom portion of the chamber portion of the apparatus of the present invention showing a push-pull valve in an opened position.

With reference to FIGS. 16-24, and more specifically with reference to FIGS. 23 and 24, there is shown one preferred embodiment of a unique and non-standard push-pull valve member 220 particularly useful with the apparatus of the present invention. The push-pull valve member 220 useful in the present invention includes a first cylindrical or tubular member of a first diameter size and comprising a wall 221 having an inner surface 221a and an outer surface 221b; and a top wall 222 integral with wall 221 at one end of the tubular wall 221. The other opposite end of the wall 221 is open and includes female threads 223 integral with the wall 221 on the inside surface 221a of wall 221 adapted to be threadably and removably attached to the male threads 216b of neck portion 216 of bag body 210. On the top wall 222 of the tubular member 221 is a circular plug member 224. The outer surface 221b of wall 221 is integral with a flange member 225 having a top surface 225a and a bottom surface 225b.

The push-pull valve member 220 useful in the present invention also includes a second cylindrical or tubular member of a second diameter size and comprising a wall 226 having an inner surface 226a and an outer surface 226b. The diameter size of the second tubular member wall 226 is larger in size than the diameter size of the first tubular wall 221 such that the outside surface 221b of wall 221 is in telescope communication with the inside surface 226b of wall 226. The second tubular member wall 226 also includes a flange member 227 having a top surface 227a and a bottom surface 227b integral with the outside surface 226b of the wall 226. The flange member 227 can be disposed near one end of the wall 226. On the other end of the tubular member wall 226 is disposed a tapered conical flange portion 228 integral with the wall 226 forming the top portion of the wall 226. The tapered conical flange portion 228 comprises tapered portion 228a, top planar portion 228b having an orifice opening 228c which is adapted for accommodating the circular plug member 224. The first tubular member 221 having a smaller diameter than the second tubular member 226 telescopes in and out of the second tubular member 226 as the push-pull valve functions to open or close the opening 228c. For example, when the push-pull valve member 220 is in a closed position, the flange member 227 is in contact with the flange member 225 such that the top wall 222 of the tubular member 221 and circular plug member 224 contact the inside surface 228a of the flange 228 to allow the plug member 224 to close off the opening 228c of the flange 228. The push-pull valve 220 of the present invention can be actuated by the actuation mechanism 50 to open or close the valve 220 as shown in FIGS. 28-33 and FIGS. 41-45.

With reference to in FIGS. 23 and 24 again, there is shown a push-pull valve member 220 useful in the present invention, and the manner of operation of the valve 220 for opening and closing the valve 220. FIG. 23 shows the push-pull valve in the closed position and FIG. 24 shows the push-pull valve in the opened position. The first tubular member 221 has an inner surface 221a and an outer surface 221b. A plurality of female threads 223 are integral with the interior surface 221a of the cylindrical portion 221 of the push-pull valve 220. The female threads 223 are used to connect the push-pull valve 220 to the body 210 of the bag 200 via the male threads 217b of the neck 217 to form a fluid-tight joint. The tubular member 221 can be slideably mounted to the tubular member 226 of the push-pull valve member 220.

When the valve 220 is in a closed position, the flange 225 integral with the tubular wall 221 can be adjacent to, and in contact with, the flange 227 integral with the tubular member wall 226. In the closed position, the bottom surface 225b of flange 225 is substantially in contact with the top surface 227a of flange 227 forming a fluid-tight coterminous boundary. The valve flanges 225 and 227 in the closed position provides a fluid-tight seal to prevent flow of fluid out of the bag body. When the valve 220 is in an open position, the flange 227 integral with the tubular member 226 can be separated from, and not in contact with, the flange 225 integral with the tubular member 221; and in turn, the plug member 224 is detached from the opening 228c. In the opened position, the bottom surface 225b of flange 225 is substantially separated from the top surface 227a of flange 227 forming a gap between the two surfaces such that the fluid-tight coterminous boundary between the two surfaces no longer exists. The valve flanges 225 and 227 in the open position (i.e., when the tapered conical flange portion 228 is pulled in a downwardly direction) allows fluid to flow freely from the bag body 210 through and out of the opening 228c.

The push-pull valve 220 is used to dispense the breastmilk from the bag 200 through the push-pull valve 220 and into the bottle 400 awaiting outside the chamber portion 10 to receive the breastmilk 300. When the bag 200 is inserted into the receptacle vessel 40 of chamber portion 10, the push-pull valve 220 is positioned toward the bottom of the receptacle vessel 40 and near the bottom of the chamber portion 10 of the dispenser 100. The bottom wall 13 of the chamber portion 10 contains an orifice opening 13a. The orifice 13a can be closed or opened using the door member 15 attached to the wall 13 of the chamber portion 10. In a preferred embodiment, the door 15 includes a top surface 15a and a bottom surface 15b; and the door 15 can be attached to the bottom wall 13, for example via a hinge member 15c such that the top surface of the door 15 closes the orifice 13a. The orifice 15 is in fluid communication with the opening 228c of the push-pull valve 220 near the bottom of the chamber portion 10. During the warm/dispense cycle and after the breastmilk reaches the target temperature, the orifice 13a is opened by opening the door member 15; and the bag push-pull valve 220 is also opened by actuating the valve actuation mechanism 50 such that the breastmilk 300 in the bag 200 can be allowed to flow freely out of the bag 200 located in the receptacle vessel 40 of the chamber portion 10, through the opening 13a and into a second container 400 (such as a baby bottle 400) located outside the chamber portion 10 and positioned under the orifice 13a. The breastmilk flow may be driven by gravity alone; or by pressure applied to the bag 200 via, for example, an air bladder 46 located in the vessel 40 when the air bladder 46 is inflated with air (described herein below in more detail with reference to FIGS. 34-40).

For a successful push-pull valve 220 function, the bag push-pull valve 220 can be located in a space near the bottom of the chamber portion 10 with the bag 200 and disposed therein in an inverted position wherein the chamfer (beveled edge, slant or shoulder) of the flange 228 of the push-pull valve 220 is seated in a matching chamfer of a tubular portion 42 of the inner conical receptacle vessel 40 near the orifice 13a at the bottom wall 13 and at the end of the tubular portion 43 of the inner conical receptacle vessel 40. The push-pull valve 220 locates radially to within a tolerance band through controlling the fit between the outer diameter of the valve and inner diameter of the tubular member 43 integral with the bottom wall 13 of the chamber portion 10.

In general, various mechanisms suitable for opening and closing the bag 200 can be used in the present invention. For dispensing breastmilk 300, for example, a preferred embodiment of opening and closing the bag 200 is carried out in a noninvasive and nondestructive manner to the bag 200 and in a non-contaminating manner to the breastmilk 300. For example, in one embodiment when the push-pull valve 220 is used as part of the bag 200 as described above, the push-pull valve 220 can be opened and closed mechanically using for example the actuation mechanism 50 (described in more detail herein below with reference to FIGS. 41-45).

In another embodiment, the push-pull valve 220 can be replaced with a "twist open" valve (not shown) which can be opened and closed using for instance a mechanically actuated twist top member which can be actuated in a rotational motion to open and close the valve. The "twist open" valve can be used to provide a means for opening the valve by mechanically rotating the valve to an open position and to allow the breastmilk fluid to flow in a downward linear flow motion from out of the chamber portion into an awaiting container 400.

In still another embodiment, the push-pull valve 220 can be replaced with a pressure valve or a pressure mechanism (not shown) which can be used to open the breastmilk bag to allow the breastmilk to flow therefrom. For example, the pressure valve can be opened using hydraulic pressure, created for example by inflating a bladder with a gas or air; the bladder located inside the chamber portion can be inflated to a predetermined pressure which in turn exerts pressure onto the flexible bag. The pressure on the bag then translates into sufficient hydraulic pressure to open the valve and allow the breastmilk in the bag to flow therefrom.

In yet another embodiment, a shear mechanism (not shown) can be used to open the breastmilk bag to allow the breastmilk to flow therefrom. In this embodiment, a small plastic piece is integrally attached to the bag. In addition, the plastic piece in this embodiment is adapted to being removed, detached, or "sheared off" from the bag in a sanitary manner. In this embodiment, for example, the small plastic piece is capable of being sheared off the bag sufficient to expose a small hole in the breastmilk bag to allow the breastmilk in the bag to flow out of the bag. For example, the small plastic piece may be a piece similar to the piece of a Kool-Aid™ Bursts bottle.

Chamber Portion

According to one embodiment of the present invention, shown in any one or more FIGS. 1-45, the chamber portion 10 of the present invention breastmilk dispenser 100 may be removably integral or permanently integral to the housing of compartment portion 20. In the embodiment shown in FIGS. 1-45, the chamber portion 10 is in special communication with the compartment portion 20, that is, the chamber portion 10 and the compartment portion 20 share at least a portion of space between each other; or in other words, a coterminous boundary between the two portions 10, 20 is simply space with air existing between the two portions.

The chamber portion 10 can be any 3-dimensional shape including a square, rectangular, cone, polygon, trapezoid, triangle, parabolic, U-shaped (horseshoe-shaped), and the like, when viewed from the top. In one optional embodiment, the chamber portion 10 may comprise, for example, an inverted and generally frusto-conical shape housing wherein the top horizontal surface plane of the top wall 12 is wider than the bottom horizontal surface plane of the bottom wall 13. In this optional embodiment, the vessel 40 can also be a generally frusto-conical shape housing receptacle vessel 40 located conterminously within the chamber housing 11 structure. In this optional embodiment, the vessel 40 can be integrally connected to the housing 11 of chamber 10; the vessel 40 and chamber 10 generally forming two concentrically-positioned frustoconical-shaped vessels wherein the vessel 40 comprises the inner frustoconical-shaped vessel and wherein the outer housing 11 of chamber 10 comprises the outer frustoconical-shaped vessel.

In the embodiment shown in FIGS. 1-45, when viewed from the top, the chamber portion 10 may be defined by a housing substantially a parabolic-shaped housing body having a sidewall 11 having a predetermined height and integral with a top proximal end wall 12 and a bottom distal end wall 13 such that the top horizontal surface plane of the top wall 12 is parallel to the bottom horizontal surface plane of the bottom wall 13 forming the inverted parabolic-shaped chamber portion 10 with the back wall of the chamber 10 (or the bottom of the parabolic shape) being formed by a portion 21a of the back wall 21 of the compartment 20.

The top wall 12 of the chamber portion 10 may constitute by a removable lid 14 having a top surface 14a and a bottom surface 14b which is connected to sidewall 11 in a hinged movement with hinge member 14c to lift the lid 14 from the sidewall 11 such that access is provided to the interior space of the chamber portion 10 and the interior space of the receptacle vessel 40. Once the lid 14 is opened, the vessel 40 is adapted for receiving the bag 200. Lifting the lid 14 allows a caregiver to gain access to the interior of the chamber portion 10/receptacle vessel 40 and to removably insert the bag 200 into the vessel 40 of the chamber portion 10. Therefore, when the lid 14 is opened, the proximal top end wall 12 is adapted to provide a means for: (1) inserting/loading a breastmilk bag 200 having a predetermined volume of breastmilk into the dispenser 100; (2) removing the breastmilk bag 200 from the breastmilk dispenser 100 when the bag 200 is emptied of its content; and (3) replacing the empty bag 200 after undergoing dispensing using the dispenser 100.

Figure 6:
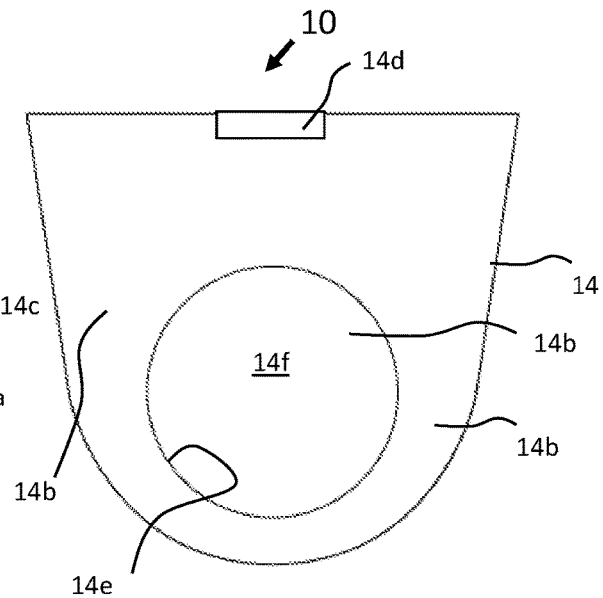
FIG. 6 is a bottom elevation view showing the bottom surface of the lid of the apparatus of the present invention shown in FIG. 1.
Figure 7:
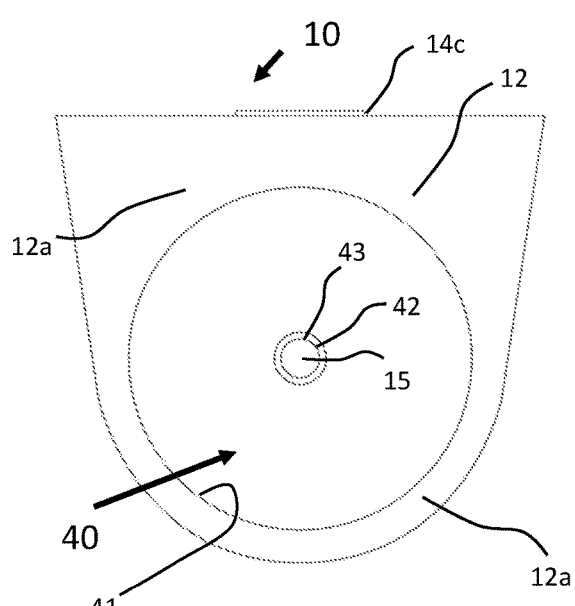
FIG. 7 is a top elevation view showing the top surface of the chamber portion without a lid and taken along line 7-7 of FIG. 2.
Figure 8:
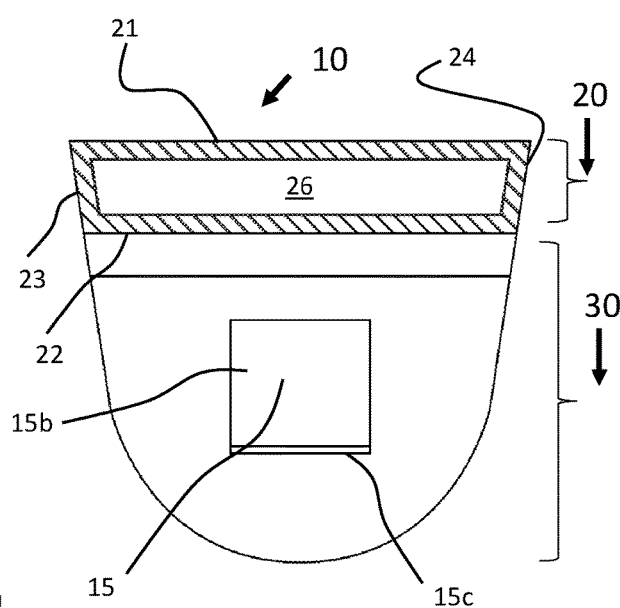
FIG. 8 is a bottom elevation view, partly in cross-section, taken along line 8-8 of FIG. 2 showing the bottom surface of the chamber portion of the apparatus of the present invention.

In one embodiment, the re-closeable cover or lid 14 on hinge member 14c as shown in FIG. 6 can be used to provide a substantially air-tight seal to the chamber portion 10 when the lid 14 is closed. Thus, the chamber of the apparatus may be air-tight or liquid sealed. Optionally, the chamber portion 10 may be completely hermetically sealed, but typically a hermetic seal is not required. In another optional embodiment, the lid 14 may include a clip (not shown) for providing extra sealing such as to provide a substantially air-tight seal when the lid 14 to the chamber portion 10 is closed. In another embodiment, the lid 14 may include threads (not shown) such that a threadable lid 14 can be removably and threadably attached to the chamber portion 10.

The bottom wall 13 of the chamber portion 10 contains an aperture or orifice 13a and a closure/opening means in the form of a re-closable cover or door 15. When the lid 14 and reclosable door 15 are in a "closed" position, a completely sealed chamber portion 10 can be provided. When the dispenser 100 is ready to use, the door 15 can be moved into the "open" position to allow breastmilk to pass through the aperture 13a when the dispenser 100 is actuated in the "on" position. Therefore, the distal bottom end 13, which includes orifice 13a that can be opened or closed utilizing a re-closeable door 15, provides a means for the breastmilk fluid 300 to: (1) exit from the bag 200 through the orifice 13a, and (2) to dispense into an awaiting second container 400. The door 15 can be attached to the bottom end wall 13 of the chamber portion 10 for example with hinges 15a. In another embodiment, the door 15 can be threadably attached to the bottom end wall 13 to cover/close the orifice 13a of the chamber portion 10 for example via male and female threads (not shown).

For storage purposes, the chamber portion 10 of the breastmilk dispenser 100 can be substantially sealed in an air-tight manner by closing the lid 14 and closing the bottom door 15 that seals the orifice 13a such that the interior of the chamber portion 10 can be: (1) closed to airborne contaminants, (2) cooled, and/or (3) warmed/heated; and thereby cooling or warming the bag 200 disposed in the receptacle vessel 40 of the chamber portion 10.

Receptacle Vessel

Figure 27:
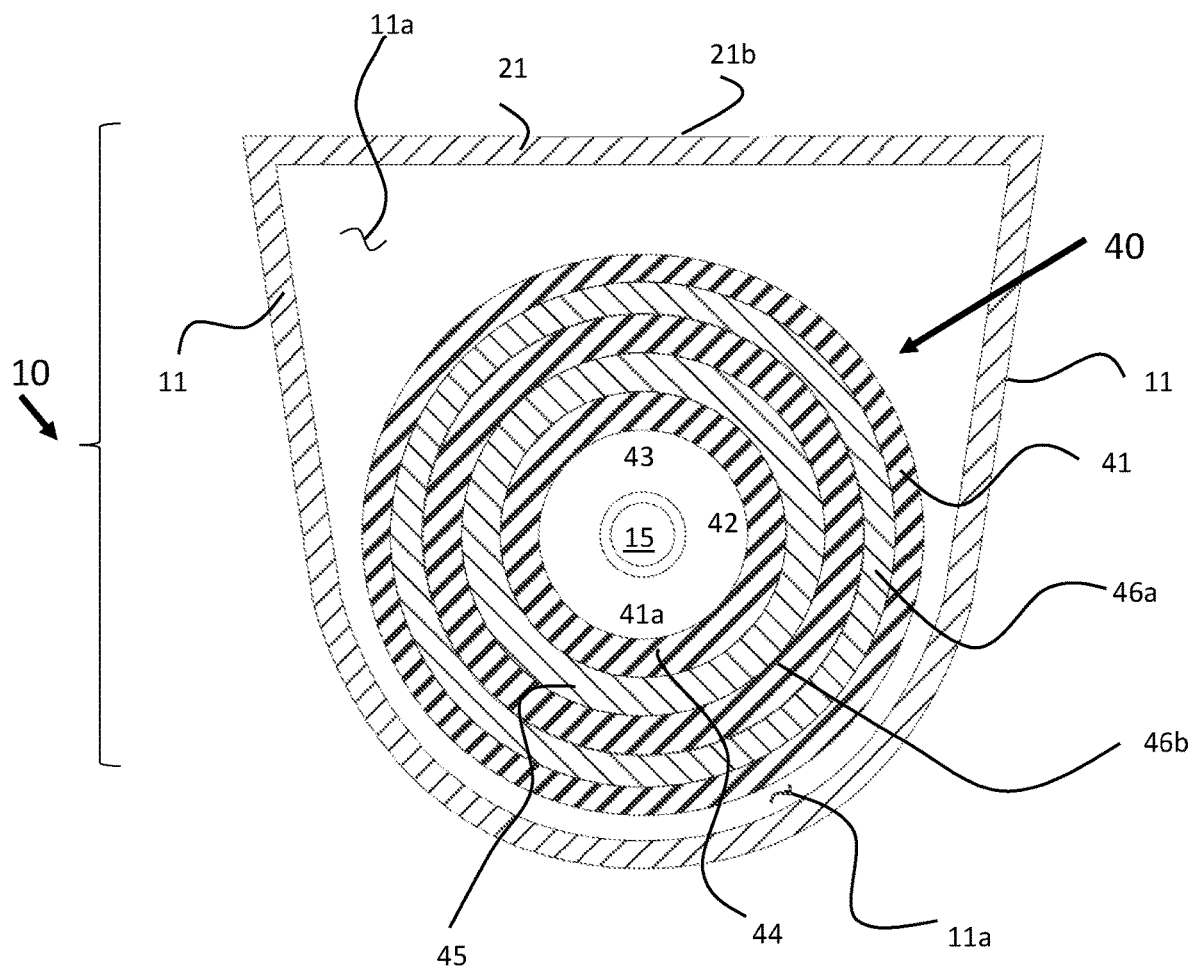
FIG. 27 is a top cross-sectional view of the apparatus of the present invention taken along line 27-27 of FIG. 2.
Figure 28:
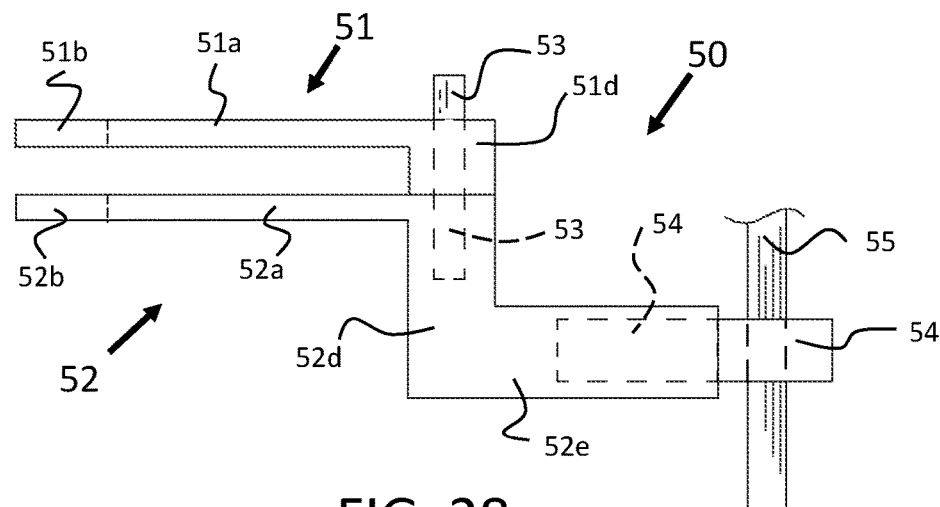
FIG. 28 is a side elevation view of a valve actuation mechanism of the present invention before the mechanism is actuated.
Figure 29:
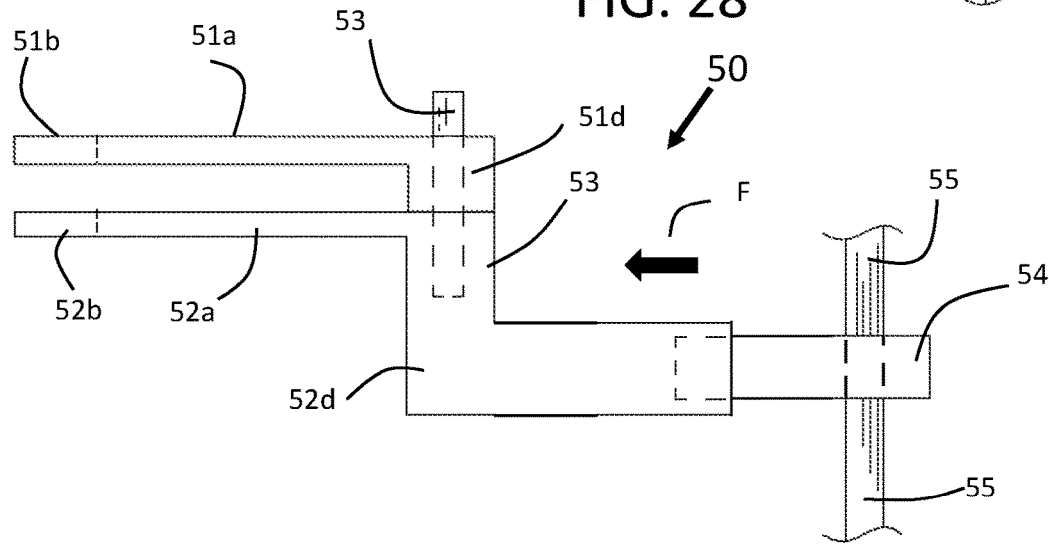
FIG. 29 is a side elevation view of a valve actuation mechanism of the present invention after the mechanism is slideably actuated in a horizontal plane direction.
Figure 30:
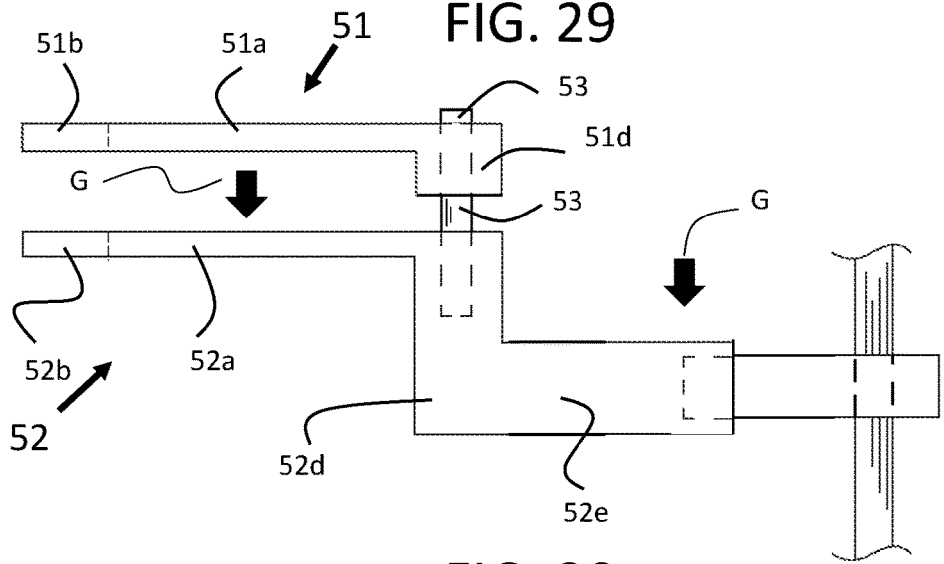
FIG. 30 is a side elevation view of a valve actuation mechanism of the present invention after the mechanism is slideably actuated in a vertical plane direction.

With reference to FIGS. 25-27, there is shown one preferred embodiment of the chamber portion 10 of the present invention comprising a pair of vessels, an inner vessel and an outer vessel where the vessels are mounted concentrically with one another leaving an annular space therebetween. A first vessel (also referred to herein as the "outer vessel") comprises the outer housing or shell 11 of the chamber portion 10. The second vessel is the receptacle vessel 40 which is a vessel of the truncated cone type, i.e., a substantially frusto-conical member. The frusto-conical vessel 40 (also referred to herein as the "inner cone" 40) comprises an inner housing or shell wall further comprising vessel portions 41, 42 and 43. The vessel 40 is concentrically enveloped by the outer housing shell 11 and is positioned coaxial with the outer shell 11; i.e., the outer side wall 11 and the inner cone wall (comprising vessel portions 41, 42 and 43) have a common axis and are concentrically arranged wherein the inner cone 40 is positioned within the outer vessel housing wall 11. In other words, the second housing or shell wall portions 41, 42 and 43 which is generally frusto-conical in shape forms the receptacle vessel 40 (the inner cone) for receiving the bag 200. In addition, shell wall of the inner cone is integrally attached, via vessel curved portion 41b, to the top proximal end wall 12 at the top horizontal surface plane 12 forming the open end 41 of the vessel 40 along the horizontal plane of the chamber portion 10. The shell wall of the inner cone 40 may also be integrally attached, via vessel tubular portion 43, to the bottom distal end wall 13 around the orifice 13a of the chamber 10.

The vessel 40 is adapted to receive the bag 200 in a vertically inverted position (see for example FIG. 34) and in a perpendicular relationship to the bottom horizontal plane of the bottom wall 13 of the chamber 10 such that the bag body 210 with push-pull valve 220 attached to the bag body 210 contacts vessel conical portion 42 located near the bottom of the receptacle vessel 40 such that bag flange 216 is seated (reposed) on the seating inner surface of valve 42 at the top proximal open end of an elongated vertical cylindrical or tubular member portion 43 integrally attached to the bottom distal end of conical vessel portion 42. The distal end of the tubular vessel portion 43 is integrally attached to the bottom wall 13. The elongated tubular portion 43 is opened at its proximal top end to receive the valve 220 in the interior space 43a of the tubular vessel portion 43; the elongated tubular portion 43 being of a length sufficient to accommodate the length of valve 220. The bottom distal open end of the tubular vessel portion 43 is attached around the circumference of the orifice 13a located in the bottom wall 13 of the chamber portion 10.

A rectangular aperture or opening 43b, located on one side wall of the elongated vertical cylindrical or tubular member portion 43, is adapted to receive the actuation mechanism 50 into the interior space 43a of the tubular vessel portion 43 such that the mechanism 50 can engage the push-pull valve 220 and open the valve 220. The valve 220 may be vertically disposed toward and near the orifice 13a such that once the valve 220 is opened by the actuation mechanism 50 and the door 15 is opened, the fluid 300 can exit the bag 200 disposed in vessel 40 of chamber portion 10 via the orifice 15.

Once the bag 200 is disposed inside the vessel 40 of the chamber portion 10 with the lid 14 closed, the interior space 11a of the chamber portion 10 can be cooled with a cooling mechanism 60 to a temperature for storing the bag 200 in a cooled environment if the feeding of the breastmilk 300 in the bag 200 will take place at a future time. Alternatively, if the feeding of the breastmilk to an infant is to take place immediately, once the bag 200 is disposed inside the chamber portion 10 with the lid 12 closed, the bag 200 disposed in the interior 41a of the receptacle vessel 40 of the chamber portion 10 can be heated by a heating mechanism 70 to bring the temperature of the bag 200 and its contents (breastmilk 300) to a temperature for feeding the breastmilk 300 to an infant. In the bottom wall 13 of the chamber portion 10, the orifice 15, in an open position (i.e., with door 15 open), allows dispensing breastmilk 300 from the bag 200 to flow through the orifice 13a and to a baby bottle 400 sitting on the base portion 30 underneath the chamber portion 10.

Actuating Mechanism

The chamber portion 10 also houses the valve actuation means or mechanism which is generally indicated by numeral 50. Once the bag 200 is disposed in the receptacle vessel 40 with the push-pull valve 220 seated in the tubular portion 43 near the opening 13a of wall 13 of the inner cone 40 located in the chamber portion 10, the valve actuation mechanism 50 can be actuated to open/close the push-pull valve 220 of the bag 200; thereby dispensing at least a portion of the breastmilk 300 from inside the bag 200. The breastmilk 300 can be dispensed into the free-standing baby bottle 400 located outside of the chamber portion 10. The baby bottle 400 is adapted for receiving at least a portion of the breastmilk 300 dispensed from the bag 200 which is disposed in the vessel 40 located in chamber portion 10.

With reference to FIGS. 28-33 and FIGS. 41-45, there is shown the valve actuating mechanism 50 disposed in the interior of the chamber portion 10 and adapted for actuating the push-pull valve 220 to an open or a closed position. The valve actuation means 50 is adapted for opening the push-pull valve 220 of the bag 200 to allow fluid 300 from the inside of the bag 200 to flow outside of the bag 200; and thus, dispensing fluid 300 from the bag 200 through the bag valve 220 upon opening the valve 220 when the actuation means 50 is actuated. The actuation valve 50 is also adapted for closing the push-pull valve member 220 of the bag 200 to prevent the fluid 300 inside of the bag 200 to flow outside of the bag 200. The valve opening/closing means 50 uniquely provides a means for dispensing fluid from the dispenser 100.

With reference to FIGS. 28-33 again, the mechanism 50 includes, for example, a first elongated guide member generally indicated by numeral 51 including a guide arm portion 51a with "finger" member portions 51b and 51c extending from the guide arm 51a and a block portion 51d which is mounted in a non-slideable manner and fixed to rod member 53. In addition, the mechanism 50 includes, for example, a second elongated guide member generally indicated by numeral 52 including a guide "arm" portion 52a with "finger" member portions 52b and 52c extending from the guide arm 52a; an elongated block portion 52d; and an elongated block portion 52e. The block portion 52d is slideably mounted to the common rod member 53 and mounted just below the guide member 51 in parallel to the horizontal plane of the guide member 51 to form a predetermined vertical gap to engage the flange members of the push-pull valve 220. The elongated block member 52e is slideably mounted to elongated block member 54, and in turn, the block member 54 is slideably mounted to rod member 55.

The arm members 51 and 52 can be moved in a linear horizontal plane direction and perpendicular to the vertical plane of the valve 220 (as indicated by arrow F) by sliding (telescoping) the block member 52e along the horizontal axis of block member 54 which is in telescope communication with the block member 52e. Upon moving the guide arm 51, the fingers 52 and 53 can engage the valve 220 (valve 220 is initially disposed in a closed position) to ready the arms 51, 52 to open the valve 220.

Once the fingers 51b, 51c and 52b, 52c of the arms 51, 52 respectively, are engaged with the flange members of valve 220, arm member 52 can be moved in a downward linear vertical plane direction and perpendicular to the horizontal plane of the push-pull valve 220 (as indicated by arrow G) by sliding (telescoping) the block member 52d along the vertical axis of the rod member 53 which is in telescope communication with the block member 52d. This vertical movement of block 52d allows arm 52 to separate a predetermined distance from arm 51 to provide an opening mechanism of the valve 220. The valve 220 once actuated to the open position allows the breastmilk 300 from the bag 200 to flow in a downward, linear, vertical plane flow direction out of the bag 200, which is disposed in the receptacle vessel 40 of the chamber portion 10, into an awaiting substantially ridge second container 400 (e.g., a baby bottle) situated on the top surface (or platform) 32 of the base member portion 30. In the embodiment shown in FIGS. 41-45, once the first container 200 is opened, the liquid fluid 300 can be allowed to flow by gravitational force from the first container 200 to expel the liquid fluid 300 from the first container 200. In another embodiment, a pressure force can be exerted against the walls of the container 200 to aid in expelling the liquid fluid 300 from the first container 200.

As aforementioned above, one important feature of the present invention is that the actuation mechanism 50 does not contact the liquid fluid 300 inside the container 200 when the actuation mechanism 50 opens the container 200 to allow the liquid fluid 300 to flow from inside the container 200 so as to maintain the liquid fluid 300 free of contamination. In one embodiment, the actuation mechanism 50 may damage or destroy a portion of the container 200 to open the container so long as the liquid fluid is not contacted by the actuation mechanism 50 (or any part thereof) and so long as the liquid fluid 300 remains pure of contamination. An example of this embodiment is described in more detail herein below.

In another embodiment of the present invention, the actuation mechanism 50, described herein below in more detail, is adapted for opening the container 200 in a noninvasive/nondestructive manner such that the integrity of the container 200 is maintained. Once the container is opened by the actuation mechanism 50, the liquid fluid 300 is dispensed from the container 200 through the dispenser orifice 15 at the bottom of the dispenser 100 and into the awaiting second container 400 disposed external to the dispenser 100. For example, the actuation mechanism 50 is adapted for opening and closing the container 200 without puncturing or tearing the wall(s) of the container 200 such that the actuation mechanism 50 does not contact/touch the liquid fluid 300 inside the container 200. Thus, the actuation mechanism 50 opens and closes the container 200, without compromising the integrity of the container 200 or the liquid fluid contents 300 of the container 200. The uncontaminated fluid 300 from the dispenser 100 is preferably dispensed into a clean and substantially sterilized second container 400.

Base Portion

With reference to FIGS. 1-11, there is shown the base portion member generally indicated by numeral 30 having a body sidewall 31, a top surface 32, and a bottom surface 33. The base portion support member 30 is adapted for supporting the chamber portion 10 and compartment portion 20 in a free-standing position. For example, the base portion member 30 is integral with and contiguous to the housing compartment portion 20 providing a base portion and support to allow the dispenser 100 to stand on its own such that the breastmilk dispenser 100 functions as a portable, free-standing apparatus. The base portion support member 30 includes a platform portion 31a integral with a compartment portion bottom portion 31b. The platform portion 31a of base portion 30 extends in a horizontal plane perpendicular to the compartment portion 20 and forms the surface 32 for receiving the second container 400. The bottom portion 31b of base portion 30 of the present invention is integral with and contiguous to the lower wall portion 21b of wall 21 of compartment portion 20.

The free-standing breastmilk dispenser 100 can be placed on top of a flat table or kitchen countertop; and operated thereon; and the base portion 30 is adapted for receiving a baby bottle 400 on the base portion's top surface 32 of the platform portion 31a for placing and positioning the baby bottle 400 underneath the chamber portion 10 such that the dispensing means dispenses and transfers the fluid 300 (e.g., breastmilk 300) from inside the bag 200 (which is in vessel 40 inside the chamber portion 10) and into the interior space of the baby bottle 400.

The bottom surface 33 of the base portion 30 may also be provided with feet or suction cups 33a to prevent the dispenser 100 from sliding on a countertop or other support surface. The housing of the dispenser 100 may be formed of a material that withstands moisture and is easily cleaned, such as stainless steel, plastic, ceramic, and the like.

In one optional embodiment, the baby bottle 400 that the breastmilk is dispensed into can be preferably resting on the horizontal flat surface 32 (also referred to as table 32) of the platform portion 31a of the base portion 30. In one embodiment, the space/gap between the bottom wall 13 of the chamber portion 10 and the top surface 32 of the base portion 30 in a vertical direction may be sufficient to accept a baby bottle of various heights. In another embodiment, the height of the table 32 can be movably adjustable, for example in a vertical plane, so as to vary the space/gap between the bottom wall 13 of the chamber portion 10 and the top surface 32 of the base portion 30 in a vertical direction to better accept bottles 400 of different sizes/heights. The table 32 of the base portion 30 can be moved vertically up or down to increase or decrease the distance between the bottom end wall 13 of the chamber portion 10 and the top of the baby bottle 400, as the case may be, such that the distance between the breastmilk push-pull valve 220 and the opening of the bottle 400 is at an appropriate distance to allow the breastmilk 300 to enter the bottle 400 without wasting breastmilk which may spill over the bottle 400.

In another optional embodiment, the flat base portion, platform, or table 30 that receives and supports the bottle in an upright position with the open end of the bottle 400 near the orifice 15 of the chamber portion 10 and that accepts and contains the warmed breastmilk may include a warming element (not shown) either embedded in the platform portion 31a of the base portion 30; or added to the top surface 32 of the base portion 30 such that the warming element can continue to warm the baby bottle 400 to a desired temperature of breastmilk and/or to maintain the desired temperature of the dispensed breastmilk in the baby bottle after dispensing until the mother or caregiver is ready to use the bottle of breastmilk to feed an infant.

In one embodiment, the platform portion 31a of the base portion 30 may include a removable drip tray 34 (shown in FIG. 10) forming the surface 32 of the base portion 30 for placing a baby bottle 400 thereon. The drip tray 34 is adapted for catching breastmilk 300 which may be spilled during the dispensing of the breastmilk from the dispenser 100. In another embodiment as shown in FIG. 11, the platform portion 31a of the base portion 30 may include a plain surface 32, without other extraneous elements, to form the surface 32 of the base portion 30 for placing a baby bottle 400 thereon.

In another optional embodiment, the table 32 of the base portion 30 may include a sensor device or element (not shown) useful for checking for the presence of a bottle 400 on the surface 32 of the platform portion 31a of the base portion 30. For example, the sensor may include a passive infrared sensor known in the art. The passive infrared sensor may be similar to the sensor commonly used on a touch-free bathroom hand dryer, a soap dispenser, or a faucet. If no bottle 400 is detected by the sensor, the dispenser 100 can be pre-programmed to not dispense the breastmilk 300 from the bag 200 inside the vessel 40 of the chamber portion 10.

Compartment Portion

With reference to FIG. 12, the housing forming the compartment portion, generally indicated by numeral 20, is integral with and coterminous to the chamber portion 10; and is integral with and coterminous to the base portion 30, thereby supporting the chamber portion 10 and compartment portion 20. The compartment portion 20 can be removably integral with or permanently integral with the chamber portion 10 and/or the base portion 30. An upper portion 21a of the housing forming part of the compartment portion 20 can be shared by a portion of the same housing forming part of the chamber portion 10 to provide intercommunication between the space in the upper portion 21a of the compartment 20 with space 11a of the chamber 10. A lower portion 21b of the housing forming part of the compartment portion 20 includes back wall 21, front wall 22, side wall 23 and side wall 24 which form a lower space 25 as shown in FIG. 10; and space 25 may also be in intercommunication with the space in the upper portion 21a.

The compartment portion 20 is adapted for containing components required for actuating and operating the functions of the machine 100. Accordingly, in the interior of the compartment portion 20 there is disposed several operational components for heating or cooling the bag 200 once the bag is loaded into the receptacle vessel 40 located in the chamber portion 10. For example, disposed in the compartment portion 20, there are several electrical components for controlling the operations of the dispenser 100. In addition, for example, the apparatus 100 of the present invention may include a cooling mechanism/refrigeration unit generally indicated by numeral 60 for cooling the chamber portion 10; and a heating mechanism/heating unit 70 for warming or thawing fluid 300 inside a bag 200 which is seated inside the receptacle vessel 40 of the chamber portion 10. The cooling and heating mechanisms can be operated in an alternative mode to cool or heat the chamber portion as desired. The compartment portion 20 can also include a pneumatic system generally indicated by numeral 80 adapted for controlling air feed to the bladder 46 disposed inside the receptacle vessel 40 of the chamber portion 10; and an electrical system generally indicated by numeral 90 including circuit boards (not shown) and power supply (not shown) well known to those skilled in the art. The electrical system 90 is adapted to energize the various control and actuation means to carry out the various functions of the machine 100 as desired.

Cooling System

With reference to FIGS. 25-27 and FIGS. 34-40, there is shown a bladder 46 positioned inside the vessel 40 of the chamber portion 10. In general, the cooling or refrigeration system 60 includes at least a first bladder 46 with walls 46a and 46b having an internal space 46c. One embodiment of the cooling system 60 useful in the present invention may include the bladder 46 adapted for receiving a volume of coolant fluid, gas or liquid, from a cooling unit (not shown) disposed in the compartment portion 20; and which is in fluid communication with the bladder 46. In one embodiment, for example, air from an air pump or other source may be used to inflate the bladder.

In another embodiment, the cooling system useful in the present invention may include a cooling unit (not shown) for cooling the space 11a around the receptacle vessel 40 such that the bag 200 is eventually brought to a desired predetermined cool temperature.

The cooling mechanism/system 60 of the present invention is preferably adapted for maintaining the bag 200 of breastmilk 300 at a consistent refrigerated temperature while the bag is being stored in the chamber portion 10. The refrigerated temperature is specified as the optimal temperature to store liquid breastmilk 300. In general, the refrigerated temperature for operating the dispenser 100 can be preset for any temperature range as desired for the selected fluid to be refrigerated. For example, a juice beverage can be set for a lower temperature versus a temperature for a coffee beverage. For storing breastmilk before heating, the refrigerated temperature of the stored breastmilk can be less than about 20° C. in one embodiment, from about −5° C. to about 20° C. in another embodiment, from about 0° C. to about 15° C. in still another embodiment, and frog about 0° C. to about 10° C. in yet another embodiment. During storage of the bag 200 in dispenser 100, the cooling mechanism/system 60 is active while the machine 100 is turned on; and the warming mechanism 70 and dispensing cycle is turned off while the cooling mechanism is active. Inversely, when the heating mechanism 70 is turned on, the cooling mechanism 60 is inactive. The dispensing cycle is activated after the desired temperature of the fluid 300 is reached and the heating mechanism 70 is inactivated.

In one embodiment, the cooling mechanism 60 may include for example a micro refrigeration unit (not shown) known in the art. The micro refrigeration unit (or typical refrigeration system) may be located in the compartment portion 20 and in general includes several components (not shown) including a compressor, an expansion valve, evaporation and condensing coils; and the cooling system is in fluid communication with the bladder 46 or the atmosphere of the internal space 11a of the chamber portion 10 such that the entire chamber portion 10 and bag 200 is cooled. The micro refrigeration unit operates similar to a common household miniature refrigerator. In other words, a small refrigeration unit can be housed in compartment portion 20 with expansion coils adjacent to the chamber portion 10. For example, a refrigeration system well known in the art can be used in the present invention such as the system described in U.S. Pat. No. 3,600,904, incorporated herein by reference. Optionally, a series of fins (not shown) forming a heat sink can be molded into the chamber portion wall to facilitate rapid heat transfer out of the chamber portion. In another optional embodiment, a thermostat (not shown) can be located within the chamber portion 10 to control the temperature inside the chamber portion 10. The compressor and expansion valve can also be located in the compartment portion 20.

In an alternative optional embodiment, a liquid cooling mechanism/system can be used to cool the chamber portion 10. The liquid cooling system may include for example a liquid sealed bladder 46 with walls 46a and 46b made of a rubber-like material for circulating a coolant, such as ice water, through the interior space 46c of bladder 46 located in the chamber portion 10 to cool the interior environment of the chamber portion 10. For example, the bladder 46 may comprise one continuous donut-shaped bladder and can be positioned around the interior or exterior surface of vessel 40. The bladder 46 with walls 46a and 46b may be for example a bladder similar to one used with a medical device that circulates ice water around a knee and that is often used after a knee injury surgery or injury. A pump (not shown) or other delivery means of the coolant may be housed in the compartment portion 20. Coolant temperature can be reduced by means of a refrigeration unit in the compartment portion 20 and then the coolant can be pumped into the bladder 46 located in the chamber portion 10. In an alternative embodiment, the same coolant and bladder system described above can be used with a liquid heating system 70.

Heating System

With reference to FIGS. 25-27 and FIGS. 34-40 again, there is shown a heating system 70 useful in the present invention including a heating element 45 positioned inside the receptacle vessel 40 of the chamber portion 10. The warming mechanism/system 70 is adapted to heat the breastmilk bag 200 with breastmilk 300 to a temperature while the bag is disposed in the vessel 40 (i.e., inner cone) of the chamber portion 10. When a warming/dispensing cycle is initiated for the breastmilk dispenser 100, the heating mechanism 70 begins to heat the breastmilk 300 from its first refrigerated temperature to a second higher predetermined target heated temperature. Once the breastmilk 300 reaches the target temperature, the breastmilk dispenser 100 dispenses the breastmilk 300 from inside the bag 200 through the orifice 13a in wall 13 of the chamber portion 10 into a baby bottle 400. The temperature of the heating element of the warming mechanism 70 is set so as to not exceed the maximum temperature for which breastmilk can be exposed to as recommended by health officials; or so as to not exceed a safe temperature for feeding an infant. In addition, the caregiver using the present invention apparatus can avoid overheating the breastmilk to ensure protection of proteins and other breastmilk components and nutrients.

There are several embodiments of the warming mechanism 70. In one preferred embodiment, for example, the warming mechanism 70 may include at least a first flexible heating element or flexible heatable heat sheet 45. Examples of a flexible heat sheet 45 useful in the present invention are described for example in U.S. Pat. Nos. 3,385,959 and 3,584,198, incorporated herein by reference. The heat sheet 45 is adapted for transferring heat to the chilled or frozen bag 200 and the breastmilk 300 inside the bag 200. The heat sheet 45 may be placed adjacent, and in contact with, the sidewalls of the bag 200. In one embodiment, the heatable element 45 may be one continuous cylindrical sheet wrapped around the interior or exterior surface circumference of the receptacle vessel 40. The temperature of the heat sheet 45 may be controlled at a temperature range to avoid exceeding a maximum temperature limit for the breastmilk 300. In a preferred embodiment, the heat sheet 45 can be both thin and flexible so the heat sheet when heated can conform to the various uneven contours of a frozen or chilled bag 200 of breastmilk. The heat sheet 45 can be made for example of thin silicone rubber. The dry heat provided by the heat sheet 45 is advantageous because the sheet 45 has none of the added complexities or disadvantages of a liquid heating/cooling system such as the possibility of leaks or bacteria build up.

In another embodiment, for example, the warming mechanism 70 may include a liquid heating system (not shown) which can be operated in a similar way as the cooling mechanism as described above except that instead of coolant passing through the interior 46c of the bladder 46 and the liquid coolant cooling the chamber portion and bag, a heated liquid is passed through the interior 46c of the bladder 46. The heated liquid in the liquid heating system 70 can be same liquid (coolant) used in the cooling system however the liquid may be warmed/heated, for example, by using heat bands or an immersion heater, and then the heat energy from the heated liquid in the bladder 46 can be transferred to the bag 200 and ultimately to the breastmilk 300 in the bag.

In one embodiment, a breastmilk temperature sensor (not shown) can be used in the chamber portion 10 such that as the breastmilk 300 is heated in the chamber portion 10, a trigger to dispense the breastmilk from the bag 200 into a bottle 400 is actuated when the breastmilk 300 reaches a desired or pre-determined temperature. The desired temperature of the breastmilk when dispensed may be either an industry-standard temperature or user-specified temperature. The temperature of the breastmilk can be measured using a contacting temperature sensor (for example, a thermocouple) or non-contacting temperature sensor (for example, an infrared thermometer). The sensor can be positioned adjacent and opposite the center of a pneumatic air cushion/bladder such that as the bladder expands, the bladder provides positive pressure against the sensor to drive direct contact (contacting sensor) or a required proximity (non-contacting sensor) with the bag of breastmilk to ultimately measure the temperature of the breastmilk.

In another embodiment, an air bladder 46 can be disposed in the space between the heat sheet and the interior surface circumference wall of the vessel 40. The bladder 46 can be inflated with air 47 from an air source (not shown) located in the compartment portion 20 of the breastmilk dispenser 100. In still another embodiment, the bladder 46 can extend around from about ½ to the full circumference of the inner cone; and in yet another embodiment, the bladder 46 can extend around at least two-thirds of the inner cone circumference. When the bladder 46 is not inflated and in a flaccid state, there is ample room in the inner cone sufficient to insert a bag of frozen breastmilk, in almost any shape, into the interior space of the inner cone. The bladder 46 in its uninflated state also eases the alignment of a bag push-pull valve 220 with the hole/orifice 13a in the bottom wall 13 of the chamber portion 10 through which the breastmilk 300 can be dispensed from the bag 200, through the hole 13a into a baby bottle 400.

Once the uninflated bladder 46 is in position in the inner cone of chamber portion 10, the bladder 46 can be inflated with air to expand the bladder 46 to place positive pressure on the heating element 45 against the frozen breastmilk bag 200. As the bladder 46 inflates, the inflated bladder 46 actuates the heating element 45 thereby forcing maximum contact between the heating element 45 and breastmilk bag 200. This increases heat transfer to the breastmilk 300. The orientation of the bladder 46 relative to a breastmilk temperature sensor (not shown) ensures that, as the bladder 46 inflates, the requisite contact or proximity is achieved between the bag 200 and sensor.

In another embodiment of the present invention (not shown), a heating system 70 for heating the bag of breastmilk may include a pump, a valve, a pressure sensor/switch and a bladder connected to an air source by flexible tubular hosing. In operation of the breastmilk dispenser, the bladder is uninflated during a storage/refrigeration cycle of the breastmilk bag; and then the bladder is inflated once the warming/dispensing cycle is initiated to warm the breastmilk bag. The bladder inflates until a pressure threshold is met. The pressure may be measured using, for example, a pressure switch or transducer. The pressure system useful in the present invention can be a very low-pressure system which may be only marginally above atmospheric pressure, and which is intended only to drive contact between the bag 200 and the heating element 45 allowing the heating element to conform to the unknown geometry of a frozen breastmilk bag. As the frozen breastmilk thaws to a liquid, the air bladder continually conforms to the normalizing shape of the bag, driving an increasing amount of contact and heat transfer. This low-pressure air bladder system maximizes heat transfer efficiency, which in turn, consequently reduces the time required to safely heat a bag of refrigerated breastmilk. The air bladder system may be additionally pressurized during dispensing of the breastmilk from the bag to aid in, and in some cases expediting, the dispensing of the breastmilk into a baby bottle 400.

In still another optional embodiment of the present invention, an air bladder (not shown) can be manufactured comprising at least two or more pneumatically independent cells in the bladder such that each individual cell can be filled with air and pressurized at differing air pressures. For example, an air bladder that is partitioned to form two independent cells can have differing air pressures in the two cells which in turn may provide different contact pressures to the bag 200. In addition, the two separately pressurized cells can provide two beneficial functions. For example, one function of the two cells (e.g., a first upper cell and a second lower cell) can include mixing of the breastmilk in the bag before the breastmilk is dispensed. It is known that as the breastmilk in the bag is heated, a temperature gradient can be created within the liquid breastmilk. To eliminate or reduce this gradient and ensure even or uniform heating of the liquid breastmilk in the bag, the two separate air cells making up the bladder may be operated with alternating high-low pressure cycles. This alternating motion, created by varying bladder volume/pressure, in turn, creates a mixing motion of the liquid breastmilk 300 inside the bag 200 as the breastmilk warms.

In yet another embodiment of the present invention, the breastmilk dispenser 100 may be turned on and off using electronic components; and the warming/dispensing cycles may be initiated through electronic controls of the electronic components. In a preferred embodiment, for example, all operating mechanisms for the breastmilk dispenser 100 are controlled using at least one or more single printed circuit boards. Electricity (power) is provided to the electronic mechanism via alternating current through an electrical cord (not shown) with a plug into a common household 110-volt electrical outlet. The electrical cord extends from the compartment portion 20 for powering the apparatus 100, such as by the household 110-volt electrical outlet. It will also be appreciated by those skilled in the art that the present invention can include an adapter such that the apparatus 100 can be powered by a cigarette lighter of an automobile, or by an alternative power source, such as a battery. Battery power may be desirable in certain other instances, such as when camping outdoors and the like.

A current market trend in the appliance industry is to connect a household appliance to the Internet. In the present invention machine, wireless communication and data transfer can be added to the machine and the user of the machine can interact with the machine by way of the Internet while geographically separated from the machine. For example, the machine can be controlled by way of a mobile application ("app"), such that the physical controls on the machine are simplified. Assuming acceptable legal/user terms of use, user data could be collected offering unprecedented consumer insights.

End Uses

As aforementioned, the dispensing apparatus of the present invention can be used for dispensing any number of liquid fluids so long as the dispensing is carried out in a sanitary manner. For example, fluids such milk, breastmilk, baby formula, juices, iced tea, water, fruit drinks, lemonade, wine, coffee, chocolate, and other liquid beverages can be dispensed using the dispenser of the present invention. In a preferred embodiment and described herein in more detail, the apparatus and method of the present invention will be described herein-after in conjunction with their use in the dispensing of breastmilk, which is desired to be dispensed in a sanitary manner.

Breastmilk

The dispenser 100 includes an assembly of elements to form a system to dispense a liquid fluid 300, hot or cold, from the first container 200 containing the fluid 300 without invasively contacting the fluid 300 in the first container 200 thereby maintaining the fluid 300 in the first container 200 uncontaminated. For example, the present invention is especially advantageous when the liquid fluid 300 in the first container 200 has to be dispensed into a second container 400 and the fluid 300 has to remain free of contaminants throughout the dispensing process from the dispenser apparatus 100 and throughout the filling process of the second container 400.

Accordingly, the liquid fluid 300 to be dispensed using the dispenser 100 of the present invention can be any beverage that requires dispensing without the beverage being tainted in any way by the liquid fluid 300 contacting parts or surfaces of the dispenser 100. For example, the liquid fluid 300 may include a liquid comestible such as hot chocolate or cocoa, hot coffee, hot tea or cold tea, water, milk, juice, soda, and the like. As previously mentioned, one preferred embodiment described herein is the use of breastmilk as the fluid 300 to be dispensed by the dispenser 100. Thus, the liquid fluid 300 to be dispensed using the dispenser 100 of the present invention will be shown and described hereinafter as breastmilk 300. However, the liquid fluid useful with the dispenser 100 of the present invention is not intended to be limited to breastmilk but shall encompass all embodiments of beverages and liquid fluids within the spirit and scope of the present invention as set forth in the appended claims.

The breastmilk 300 dispensed by the dispenser 100 is used for feeding an infant; and because of the obvious importance of breastmilk 300 as nourishment for an infant, the breastmilk 300 is desired to be kept in its pure form without the breastmilk 300 or its nutrients being tainted such that an infant can receive the benefits of consuming breastmilk 300.

Breastmilk 300 is a natural nutritious food for an infant; and unlike infant formula, breastmilk 300 does not have to be mixed with water or other fluid before feeding the breastmilk to an infant. Although breastmilk can be fed to an infant directly to the infant from a mother's breast, this may not always be possible. For example, when an infant has to be fed on-demand at various hours of the day or night and the mother is not available to feed the infant; for example, when a mother is at work and an infant caregiver is watching the infant at home, breast feeding breastmilk to an infant may not be convenient or possible. Therefore, in such instances where the mother and infant are physically apart at a time when an infant requires feeding, a substitute for breastmilk is typically infant formula. However, if a mother wishes to provide breastmilk to her infant at a time when the mother is apart from the infant, a supply of breastmilk has to be "harvested", i.e., collected in a container and the container with breastmilk has to be stored in a refrigerator or freezer until such time as an infant requires feeding, i.e., the stored breastmilk can be on-hand and available for feeding an infant on-demand at a later time.

Breast Pump

Generally, when a mother is not able to feed an infant from the mother's breast in present time, the breastmilk 300 can be pumped or expressed from a mother's breast using, for instance, a breast pumping unit or "breast pump" (not shown). Harvesting, collecting or expressing breastmilk from a mother's breast is carried out using a breast pump prior to operating the breastmilk dispenser 100 of the present invention. Several breast pumps for pumping breastmilk and harvesting breastmilk for later use are well known in the art. Such pumps may be operated manually or mechanically driven. For example, breast pumps for harvesting breastmilk are described in U.S. Pat. Nos. 7,413,557; 7,749,188; 8,075,516; 8,079,975; 8,142,392; and 8,591,458B2; U.S. Patent Application Publication No. US202/0156419A1; and JP2001299905A, all of which are incorporated herein by reference.

Breastmilk Harvesting

Typically, a conventional process of harvesting, collecting or expressing breastmilk includes the steps of: (a) attaching a breast pump to a mother's breast; (b) pumping, using the breast pump, a volume of breastmilk from the mother's breast into an intermediary collection container; (c) transferring the breastmilk from the collection container to an impermeable storage container; (d) closing/sealing the storage container; and (e) freezing or refrigerating the closed storage container containing the breastmilk in a freezer or refrigerator for later use.

In general, the process of the present invention for harvesting breastmilk includes the steps of: (a) attaching a breast pump to a mother's breast; (b) pumping, using the breast pump, a volume of breastmilk 300 from the mother's breast to a flexible flaccid impermeable bag 200; (c) fitting the bag 200 with a push-pull valve 220 to close the bag 200; and (d) freezing or refrigerating the closed storage bag 200 containing the breastmilk 300 in a freezer or refrigerator for later use. In this embodiment of the present invention, the breastmilk bag 200 (shown in FIGS. 16-22) used for storing breastmilk 300 can be the same bag/container used for collecting breastmilk 300; and the bag 200 is adapted for receiving/containing the breastmilk 300 expressed from a mother's breast using the breast pump. By transferring the expressed breastmilk 300 from the mother's breast into the bag 200, step (c) of the above conventional process is eliminated, i.e., there is no need to include an additional handling step of transferring the breastmilk 300 from a first standard container attached to the pump to a second, separate and different, standard storage container for storage. In addition, by connecting the bag 200 to a breast pump and pumping breastmilk from a mother's breast into the breastmilk bag 200 using the breast pump, the sanitation of the breastmilk can be more easily maintained, and the time and cost of using the process and apparatus of the present invention can be reduced, for example, by removing the intermediary collection container.

Bag/Pump Adaptor

The bag 200 for collecting breastmilk may include a means for releasably attaching the bag 200 to a breast pump (which, in turn, is attached to a mother's breast). For example, the breastmilk bag 200 used in the present invention may be: (i) connected directly to a pumping device or breast pump (not shown) to allow the breast pump to pump breastmilk 300 directly from the breast into the breastmilk bag 200; or (ii) fitted with a coupling member/adaptor (not shown) to connect the bag 200 to one end of the adaptor and to connect the breast pump to the other end of the adaptor allowing the breastmilk to flow from the breast through the adaptor and into the bag 200. In either embodiment described above, the breastmilk 300 collected in bag 200 can be stored for later use in the dispenser 100 of the present invention.

In one embodiment, the expressed breastmilk 300 may be transferred directly from the mother's breast into the bag 200 thereby eliminating a step of transferring the breastmilk) from a first standard container attached to the pump to a second, separate and different, standard storage container for storage. In this embodiment for example, the bag 200 can be removably connected to the outlet of the breast pump (e.g. a transfer hose of the breast pump), and when the breast pump is activated, the resulting pumped (or expressed) breastmilk 300 may be directly conveyed into the bag 200. The bag 200 may be connected to the breast pump for example by threadably connecting the neck portion 217 of the bag body 210 of the bag 200 having male threads 217b to a breast pump having female threads for receiving the male threads 217b.

After the breastmilk 300 is pumped into the bag body 210 and the bag 200 is filled with expressed breastmilk 300 in the bag body 210 (i.e., the breastmilk 300 is contained inside the liquid-containing portion of the bag 200), the breastmilk bag 200 can be detached directly from the breast pump. Then, the detached breastmilk bag 200 can be removably attached to a cap (not shown) for covering the opening 217a; or to the push-pull valve 220 for sealing/closing the opening orifice 217a of the bag body 210. For example, a push-pull valve 220 can be screwed onto the male threads 217b of the neck portion 217b to close the opening 217a of the breastmilk bag body 210 such that the breastmilk bag 200 can be sealed liquid-tight. The liquid sealed bag 200, with filled breastmilk 300, can then be used as a storage container for storing the bag/breastmilk, that is, the bag 200 can be placed in a freezer or refrigerator for storage until the breastmilk 300 is ready for preparation and feeding to an infant.

In another embodiment of the present invention, the bag 200 can be first removably connected to a coupling member/adaptor (not shown) and then the adaptor can be removably connected to a breast pump. In this alternative embodiment, the adaptor can be attached to the breast pump and bag 200 to provide fluid communication between the breast pump and the bag 200. For example, the threaded neck portion 217 of the bag body 210 of the bag 200 having male threads 217b on the neck 217 can be threadably connected to one end of the adaptor having female threads for receiving the male threads 217b of the threaded neck portion 217; and the breast pump (selected from any number of known breastmilk pump models) can be connected to the other end of the adaptor opposite the bag body 210.

After the breastmilk 300 is pumped into the bag body 210, the bag body 210 is removed from the coupling/adapter and breast pump. Then, a cap member (not shown) with female threads or a push-pull valve 220 with female threads can be screwed onto the male threads 217b of the neck portion 217 to close the opening 217a of the breastmilk bag body 210 such that the breastmilk bag 200 can be sealed liquid-tight. The liquid sealed bag 200, with filled breastmilk 300, can then be stored in a freezer or refrigerator for later use.

Ancillary Equipment

Other optional embodiments of the present invention may include ancillary equipment that can advantageously be used with the breastmilk bag 200. For example, a freezer tray (not shown) adapted for receiving one or more flexible breastmilk bags 200 may be used to hold one or more breastmilk bags 200 in an orderly arrangement before the bag(s) are placed in a freezer or refrigerator to be frozen or cooled. The tray can be any shape. For a single bag 200, the tray can be rectangular in shape to hold a bag 200 which, after being filled with breastmilk, is typically in a rectangular pillow shape. For a plurality of bags 200, the freezer tray may comprise a plurality of rectangular individual cells or spaces in the shape of the pillow-shaped bags to receive the bags such that the bags, in the bags' flexible state, can conform to the shape of the tray cells in an organized manner, for example, before the bags are placed in a freezer to be frozen. When the breastmilk bags freeze in the tray, the bags freeze in the shape corresponding to the rectangular tray shape cell. The above embodiment of freezing a breastmilk bag in a freezer tray has the advantages of being ideal for being frozen into a shape that can be easily placed into the receptacle vessel 40 of the chamber portion 10 of the dispenser 100 and that can be heated in the vessel 40 in a time-efficient manner.

Breastmilk Preparation

When a baby is ready to be fed breastmilk 300, a mother or a baby caregiver remove the bag 200 from storage, that is, the bag 200 may be removed from a refrigerated environment (for example a refrigerator appliance or freezer appliance) and then the bag containing chilled or frozen breastmilk can be inserted into the receptacle vessel 40 inside the chamber portion 10 of the present invention breastmilk dispenser apparatus 100 to warm or thaw the frozen bag 200 which, in turn, warms or thaws, the breastmilk 300 inside the bag 200. However, the bag when placed in the dispenser 100 does not have to be warmed right away, but instead, can remain in the dispenser 100 because the dispenser has the capability of continuing cooling the bag 200 at a predetermined cooling temperature until such time that an infant is ready to be fed. Thus, on-demand, the bag can be placed in the chamber portion 10 of the breastmilk dispenser 100, and then further cooled in the dispenser 100 and maintained at a cooled temperature until such time that an infant is ready to be fed. At such feeding time, the cooled bag is heated or warmed to bring the temperature of the breastmilk up to a temperature (e.g. room temperature) such that the breastmilk can be fed safely to an infant. In general, the temperature for operating the dispenser 100 can be preset for any temperature range as desired for the selected fluid to be heated. For example, coffee can be set for a higher temperature versus a temperature for a juice beverage. For safely feeding breastmilk to an infant and for maintaining the integrity of the nutrients, the heated temperature of dispensing breastmilk can be in the range of from about 20° C. to about 40° C. in another embodiment, from about 25° C. to about 37° C. in still another embodiment, and from about 27° C. to about 35° C. in yet another embodiment.

Alternatively, the cooled bag 200 can be heated, to the temperatures described above, immediately after placing the bag 200 in the dispenser 100 so as to prepare the breastmilk 300 for feeding the breastmilk 300 to an infant as described herein.

Dispenser Operation

In one optional embodiment of the present invention, the dispenser 100 may include a means (not shown) for sensing the volume of breastmilk in the bag 200 that is positioned inside the dispensing chamber portion 10. For example, the volume and pressure of air in the air bladder 46 can be measured by an air pressure measuring device (not shown), and then any remaining volume within the chamber portion 10 not taken by the air bladder 46 can be calculated and such volume can be correlated to a theoretically calculated bag volume. The dispenser 100 can provide this advantageous benefit since conventional dispensing machines are not capable of sensing the volume of breastmilk in a bag that is loaded inside a dispensing chamber portion.

In another optional embodiment, the apparatus of the present invention may include a display means or an indicator means (not shown) such as for example LEDs for numerically indicating various data including for example: (i) the fill status of bag 200 inside the chamber portion 10, (ii) the temperature inside the chamber portion 10, (iii) the temperature of the bag 200, and (iv) the temperature of the bottle 400, among other data and the like.

In still another optional embodiment, the apparatus 100 of the present invention may include a substantially transparent window (not shown) built into the wall 11 of the chamber portion 10; which is adapted for viewing (or visually inspecting) the bag 200 inside the chamber portion 10 and visually determining the fill status of the bag 200 in the chamber portion 10. The window or sight glass is generally disposed in the chamber and is adapted for visually monitoring the container of breastmilk as the frozen solid breastmilk transforms into a volume of fluid liquid breastmilk.

The fluid (e.g., breastmilk) in the container such as bag 200 can be dispensed from the breastmilk-containing bag 200 by opening a valve that is integral with the bag during a dispensing cycle. However, during the entire dispensing cycle, the breastmilk should not come into contact with any machine component. Accordingly, in one preferred embodiment of the present invention, the fluid in the container 200 can be dispensed from the container in a noninvasive and nondestructive method. Noninvasive/nondestructive dispensing is important when the fluid is a fluid that should not be contaminated in any way. For example, breastmilk should not contact any equipment or human hands as the fluid travels from the bag 200 to the second container 400 via the dispenser apparatus 100 such that the breastmilk can be pure when an infant ingests the fluid. The dispensing apparatus 100 of the present invention is beneficially adapted for dispensing fluid such as breastmilk without the breastmilk being contaminated.

In general, to ensure that no breastmilk contacts any machine components of the dispenser, the opened push-pull valve 220 may need to extend a slight distance proud of the outer bottom face of the chamber portion i.e., protrudes slightly beyond the bottom surface of wall 13 of the chamber portion 10. In the embodiment shown in FIGS. 34-40, the push-pull valve 220 is positioned just inside the interior space 43a of tubular portion 43 of the receptacle vessel 40 and as near as possible to the top surface 15a of the door 15. The valve can be opened once the target breastmilk temperature is reached. The operation of opening the valve of the push-pull type and design may vary. However, any valve type and design can be used provided that the mechanical operation of the valve allows the breastmilk 300 in the bag 200 to flow into a baby bottle 400 without contacting any components of the breastmilk dispenser 100.

For example, the apparatus 100 via the vessel 40 of the chamber portion 10 can receive the breastmilk storage bag 200 containing breastmilk 300; and the dispensing apparatus 100 can then subsequently dispense the fluid breastmilk 300 from the storage bag 200 into the interior housing of the free-standing container 400 disposed externally to the apparatus 100 (for example, the baby bottle 400). During dispensing of the breastmilk 300 from the appliance 100, the breastmilk 300 does not intentionally contact any dispenser equipment or human hands. The baby bottle 400 is placed on the top surface 32 of the platform portion 31a of the base portion 30 in the space between the bottom wall 13 of the chamber portion 10 and the top surface 32 of the base portion 30. The bottle 400 remains external to, but adjacent to, the breastmilk dispensing apparatus 100 underneath the orifice 13a of the bottom wall 13 of the chamber portion 10. When the breastmilk is dispensed from the chamber portion 10, the bottle 400 is positioned underneath the flow of breastmilk from the chamber portion 10 to catch and hold the breastmilk in the bottle 400 without the breastmilk 300 ever intentionally contacting any dispenser equipment or human hands of the operator or infant caregiver. The fluid breastmilk 300 thus advantageously remains uncontaminated, non-adulterated and as sterile as possible.

With reference to FIGS. 13-15, there is shown a general sequence of side views of the dispensing apparatus 100 in its various stages of operation. For example, in FIG. 13, the housing forming the chamber portion 10 is shown in a sealed or closed position in a non-operational mode prior to receiving a first container 200 such as a flexible, fluid storage bag 200 shown in FIG. 13. In FIG. 13, the chamber portion 10 is shown in an opened position with the chamber portion top lid 14 being unlatched. The bag 200 can then be inserted into the receptacle vessel 40 (not shown in FIG. 13) of the chamber portion 10 as shown in FIG. 13. In FIG. 14, there is shown the chamber portion top lid 14 closed and the chamber portion 10 resealed with the bag 200 disposed inside the vessel 40 (not shown in FIG. 14) of the chamber portion 10. Once the bag 200 is enclosed in the vessel 40 of the chamber portion, the chamber portion 10 may be used for any one or more functions including storing, heating, cooling, and/or messaging (for mixing the bag contents) the bag 200 and subsequently dispensing a fluid 300 from the bag 200. The second free-standing container 400 (such as a baby bottle 400) can be placed juxtaposed underneath the chamber portion housing for collecting/capturing any dispensing the fluid 300 exiting the chamber portion 10 through there-closable orifice 13a in the bottom wall 13 of the chamber portion 10 as shown in FIG. 15.

The actuation of the delivery of breastmilk may be triggered by an actuation button means (not shown) which activates the actuation mechanism 50 to open the push-pull valve opening/closing means 220. The process of dispensing the breast milk includes the step of actuating, in a noninvasive manner, the valve of the push-pull valve of the first container (bag 200) into an open position such that the fluid in the first container flows through the opening in the valve to allow the contents of the first container to flow out of the first container into a second container (baby bottle 400).

In one embodiment of operation, the lid 14 of chamber portion 10 is opened, the bag 200 is inserted into the chamber portion 10, the lid 14 and closure 15 are sealably closed to form a substantially air tight seal of the chamber portion 10, and then the "on" button is actuated to actuate the actuation mechanism 50 to place the push/pull valve 220 in an open position such that the breastmilk 300 can begin flowing from the vessel 40 of the chamber portion 10 through the aperture 13a and into the baby bottle 400. When the flow of fluid is complete or a predetermined amount of breastmilk 300 is dispensed into the baby bottle 400, an "off" button is actuated to a "shut off" position which then activates the actuation mechanism 50 to place the valve 220 to a closed position and to stop the flow of breastmilk 300 from bag 200.

Receptacle Vessel Operation

Figure 34:
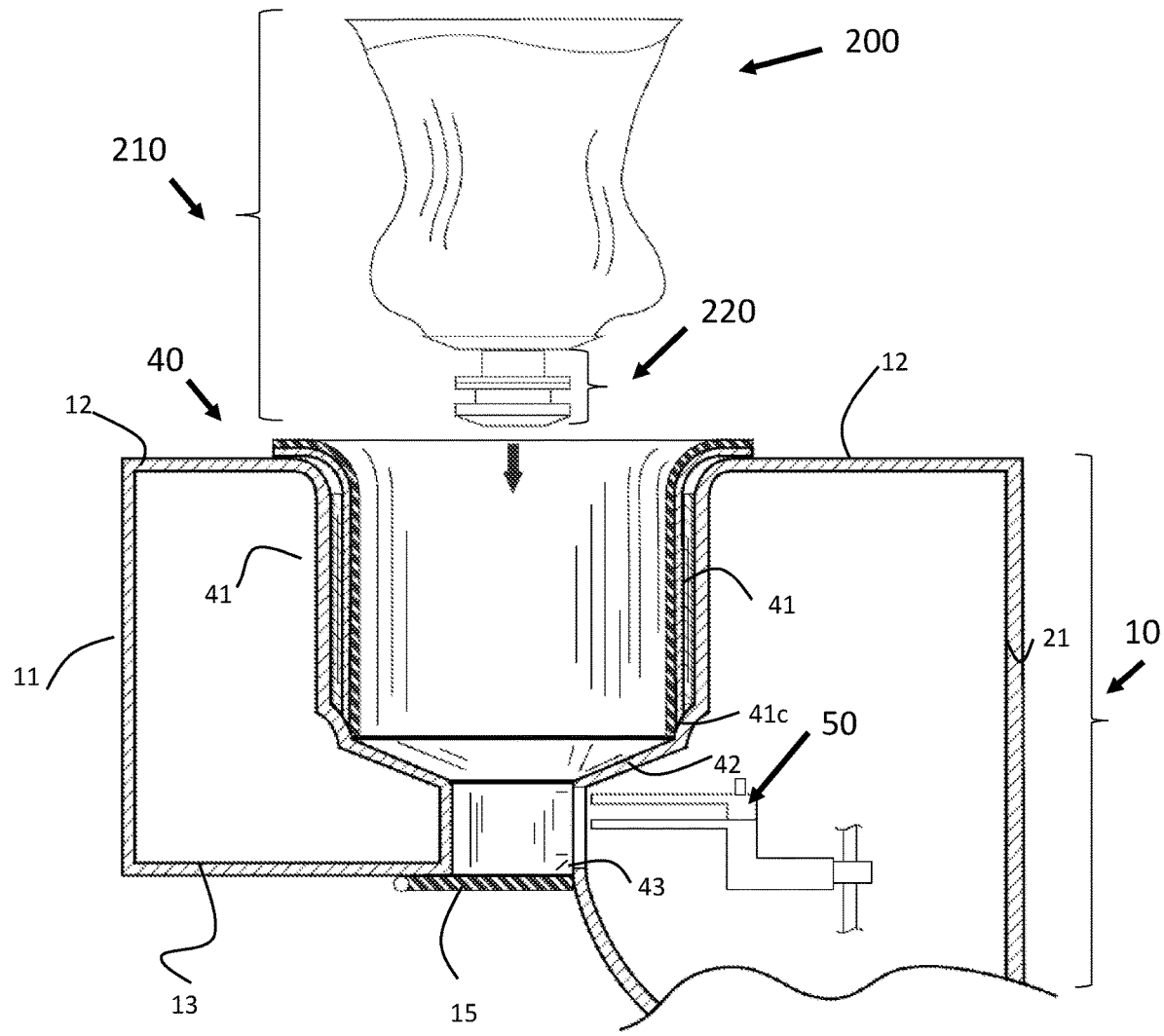
FIG. 34 is a side elevation view, partly in cross-section and partly broken away, of the chamber portion of the apparatus of the present invention showing an empty receptacle vessel of the chamber portion without a lid and receiving a frozen bag.

With reference to FIGS. 34-40, there is shown in more detail the heating sequence of a frozen bag 200 while disposed in the receptacle vessel 40. In FIG. 34, there is shown a bag 200 being inserted into the internal space 41a of the receptacle vessel 40 located in the chamber portion 10 of the apparatus 100 of the present invention. FIG. 34 shows an empty receptacle vessel 40 of the chamber portion without a lid and receiving a frozen flexible bag 200 with the outer surface of the flexible bag 200 not yet contacting the liner 44 located in the inner wall of the receptacle vessel 40. The bag in this embodiment is being inserted into the receptacle vessel 40 in a downward vertical plane direction.

Figure 35:
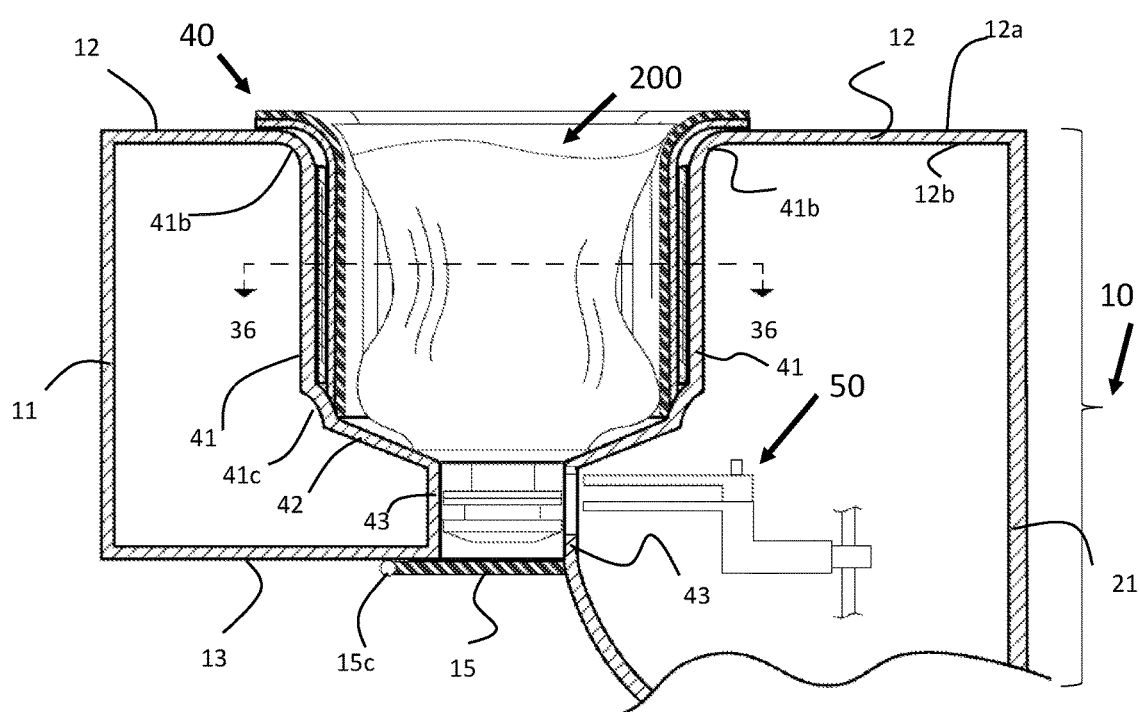
FIG. 35 is a side elevation view, partly in cross-section and partly broken away, of the chamber portion of the apparatus of the present invention showing the receptacle vessel of the chamber portion without a lid and a frozen bag disposed therein.
Figure 36:
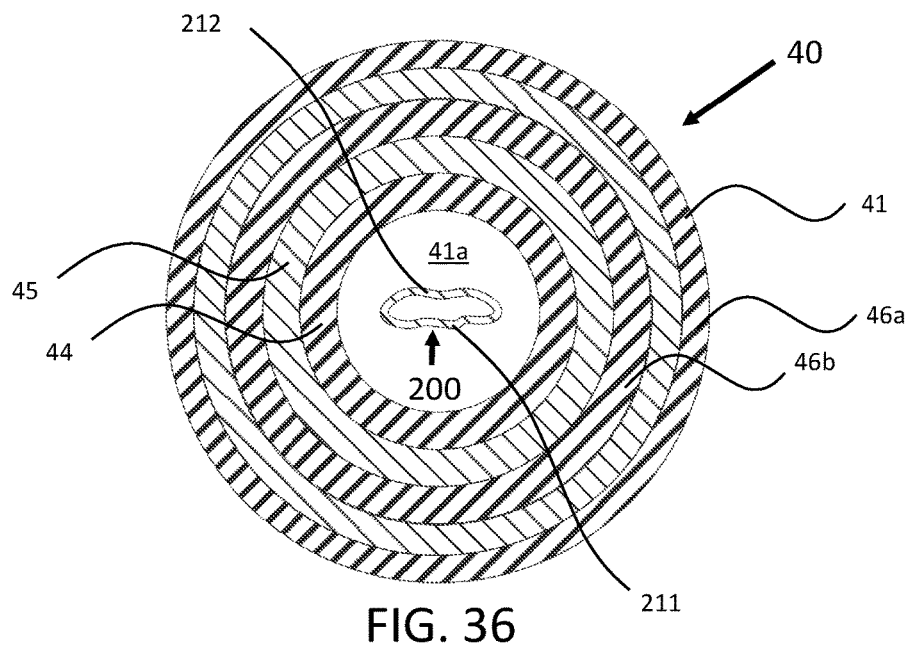
FIG. 36 is a top cross-sectional view taken along line 36-36 of FIG. 35.

With reference to FIGS. 35 and 36, there is shown a bag 200 seated in the internal space of the receptacle vessel 40 of the chamber portion 10 of the apparatus 100 of the present invention. FIGS. 35 and 36 further shows the receptacle vessel 40 of the chamber portion 10 without a lid 14; a cooled or frozen flexible bag 200 disposed in the receptacle vessel 40 with the flexible bag 200 outer body surface not yet completely in contact with the liner 44 located in the inner wall of the receptacle vessel 40; an uninflated air bladder 46 disposed in the receptacle vesse 401; and the neck and shoulder of the flexible bag 200 seated in the bottom conical portion 42 of the receptacle vessel 40. The receptacle vessel 40 of the chamber portion 10 is shown with an uninflated bladder 46.

Figure 37:
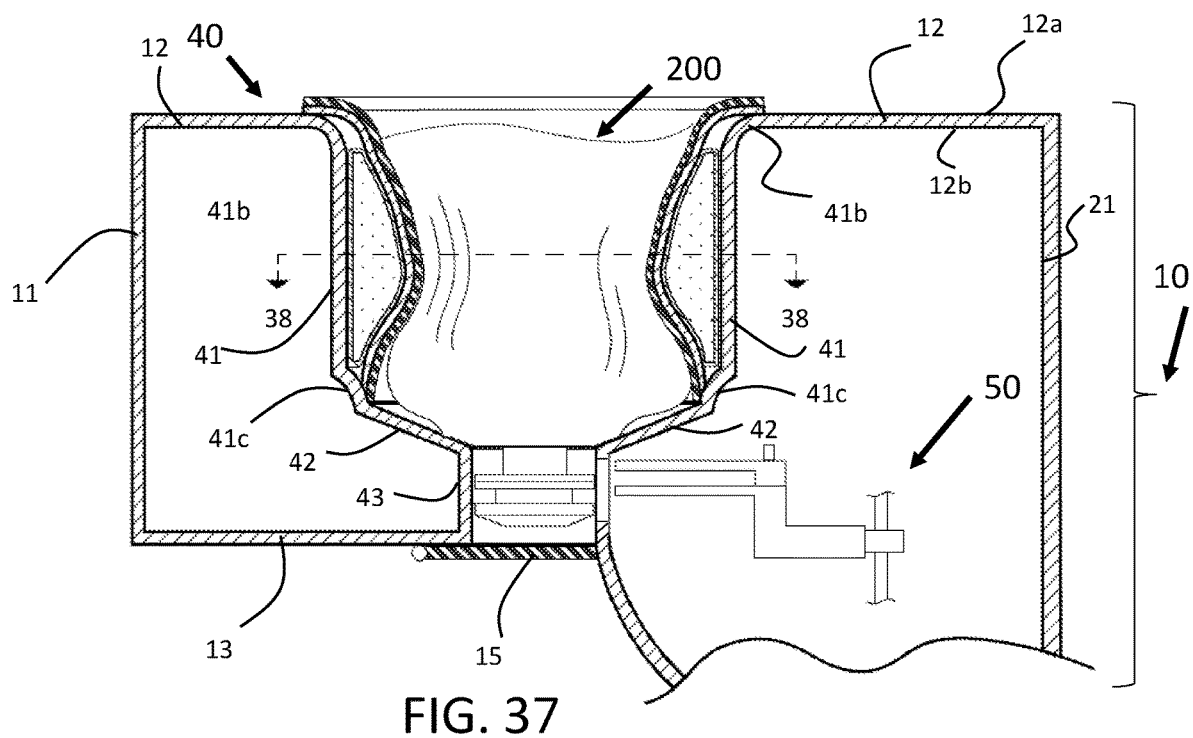
FIG. 37 is a side elevation view, partly in cross-section and partly broken away, of the chamber portion of the apparatus of the present invention showing: the receptacle vessel of the chamber portion without a lid, a frozen bag disposed therein, and an inflated air bladder.
Figure 38:
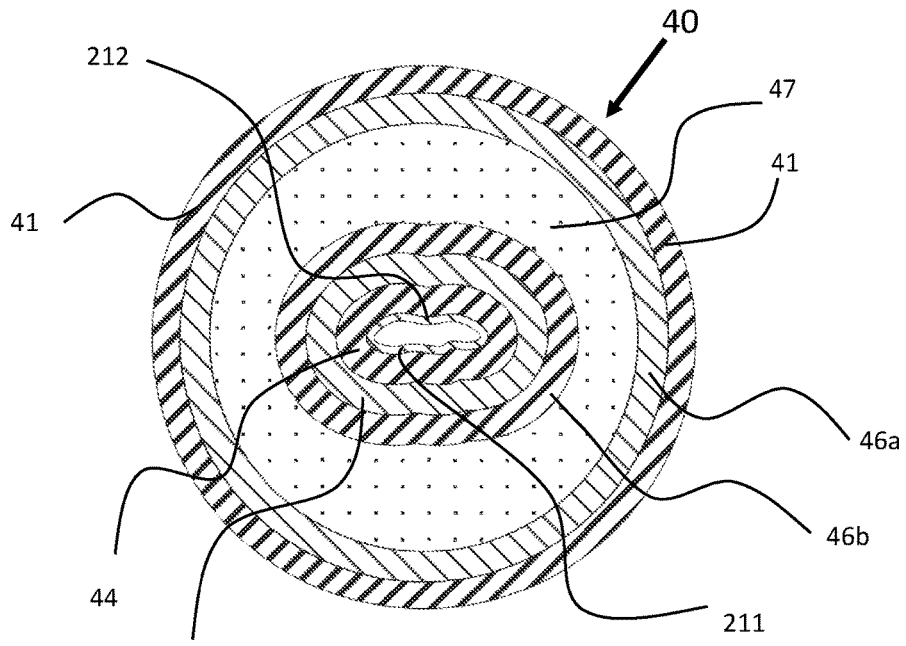
FIG. 38 is a top cross-sectional view taken along line 38-38 of FIG. 37.

With reference to FIGS. 37 and 38, there is shown is a bag 200 inside the chamber portion 10 of the dispenser 100. FIGS. 37 and 38 further show the receptacle vessel 40 of the chamber portion 10 without a lid 14; a cooled or frozen flexible bag 200 disposed in the receptacle vessel 40; a heating film element 45; and an inflated air bladder 46 inflated with air 47 to provide pressure against the heating film element 45 and the liner 44 located in the inner wall of the receptacle vessel 40 which, in turn, provides contact between at least a portion of the surface contour of the bag 200 with at least a portion of the surface contour of the heating film element 45 and liner 44. The receptacle vessel 40 of the chamber portion 10 is shown with a bladder 46 inflated with air 47.

Figure 39:
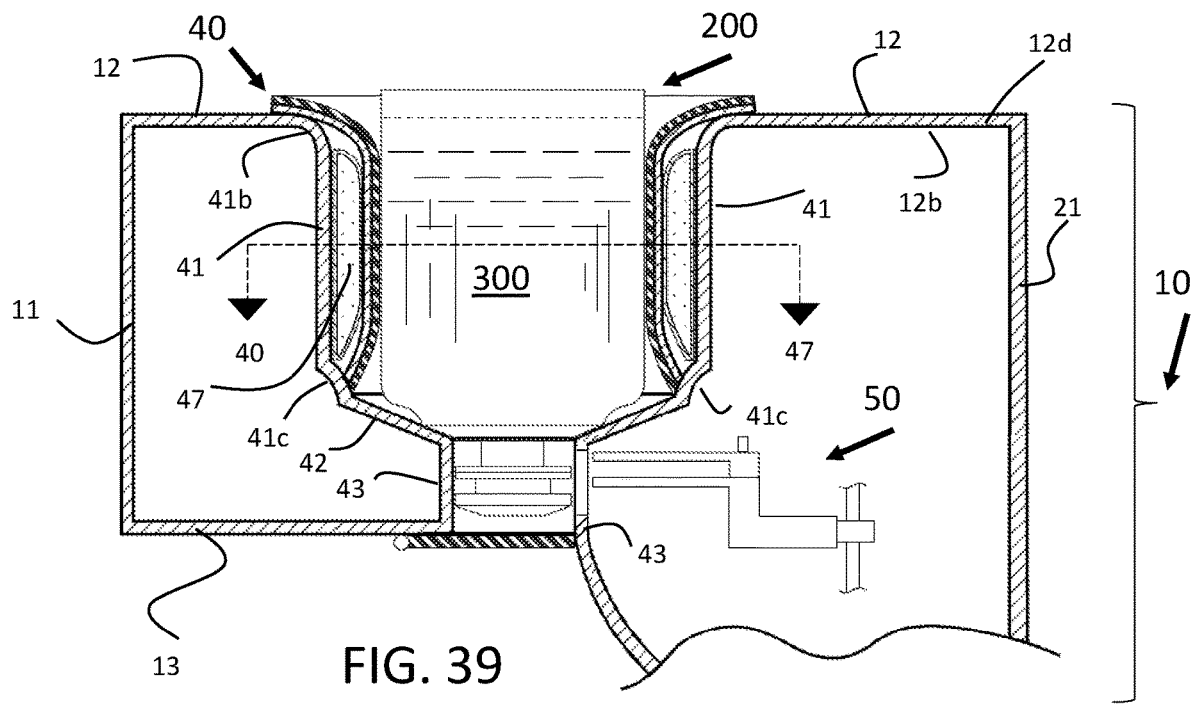
FIG. 39 is a side elevation view, partly in cross-section and partly broken away, of the chamber portion of the apparatus of the present invention showing: the receptacle vessel of the chamber portion without a lid, a thawed out flexible bag disposed therein, and an inflated air bladder.
Figure 40:
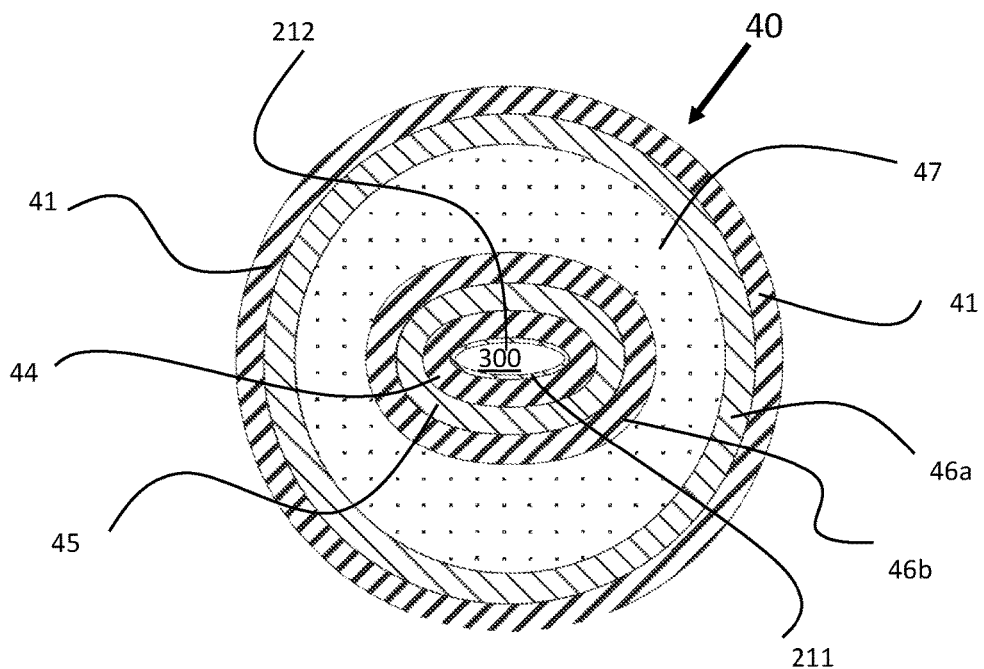
FIG. 40 is a top cross-sectional view taken along line 40-40 of FIG. 39.

With reference to FIGS. 39 and 40, there is shown a completely thawed bag 200 inside the internal space of the vessel 40 of the chamber portion 10 of the dispenser 100. FIGS. 39 and 40 further show the receptacle vessel 40 of the chamber portion 10 without a lid 14; a thawed out flexible bag 200 disposed in the receptacle vessel 40; a push-pull valve 220 coupled to the flexible bag 200 in a closed position; a liquid fluid 300 inside the interior space of the flexible bag 200; and an inflated air bladder 46 inflated with air 47 to provide pressure against the heating film element 45 and the liner 44 located in the inner wall of the receptacle vessel 40 which, in turn, provides contact between at least a portion of the surface contour of the bag 200 with at least a portion of the surface contour of the heating film element 45 and liner 44. Also present in FIGS. 39 and 40 are a valve actuation mechanism 50 set in a non-actuated, non-engagement position with the push-pull valve 220; a bottom door 15 of the chamber portion 10 in a closed position; and no fluid 300 flowing out of the flexible bag 200. The receptacle vessel 40 of the chamber portion 10 includes the thawed out flexible bag 200 disposed in the receptacle vessel 40 with a liquid fluid 300 inside the interior space of the flexible bag 200 with a bladder 46 inflated with air 47 to maintain pressure on the fluid 300 in the bag 200 before the fluid 300 is dispensed from the bag 200. At the point when the bag 200 is at the appropriate temperature for dispensing, the bag 200 is ready to be opened with the actuation mechanism 50.

Actuation Mechanism Operation

Figure 41:
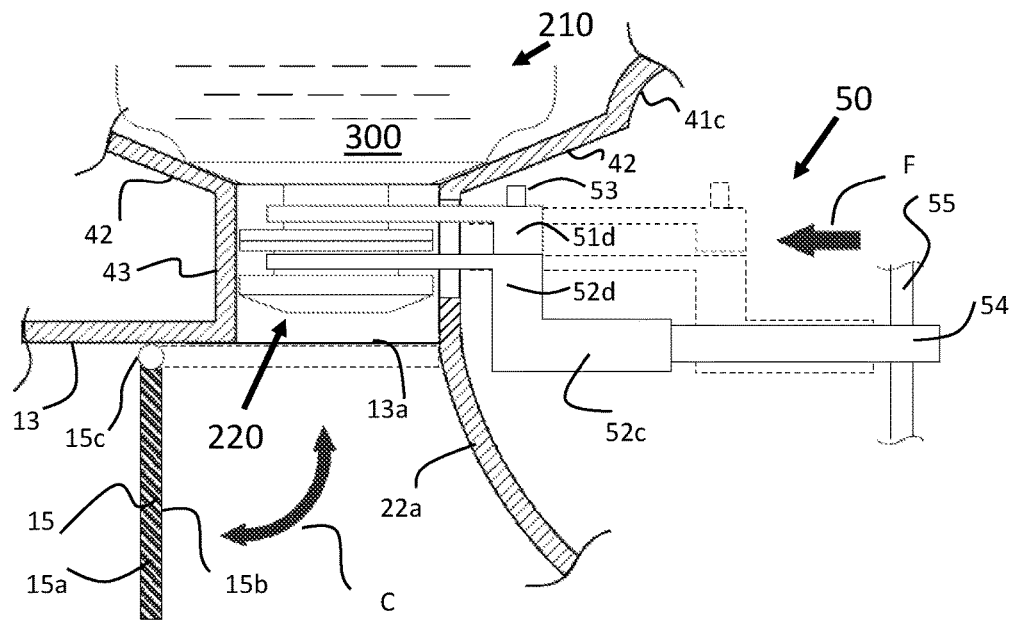
FIG. 41 is a magnified side elevation view, partly in cross-section and partly broken away, of the bottom portion of the receptacle vessel of the chamber portion of the present invention showing a push-pull valve in a closed position; a valve actuation mechanism in an actuated, engagement position with the push-pull valve; and the bottom door of the chamber portion in an open position.

With reference to FIGS. 41-45, there is shown in more detail a sequence of the activation of the actuation mechanism 50 to open and close the thawed-out bag 200 while disposed in vessel 40. FIG. 41 shows the bottom portion of the receptacle vessel 40 of the chamber portion 10 of the present invention. While the push-pull valve is in a closed position before the push-pull valve of the bag is opened, the actuation mechanism 50 can be moved in the direction of the arrow F to engage the push-pull valve 220 and to set the mechanism 50 in a position to open the valve. When the actuation mechanism 50 has moved in a horizontal plane direction as indicated by arrow F and engaged the push-pull valve in a closed position, the bottom door 15 of the chamber portion 10 is moved in the direction as indicated by arrow C to open the door 15.

Figure 42:
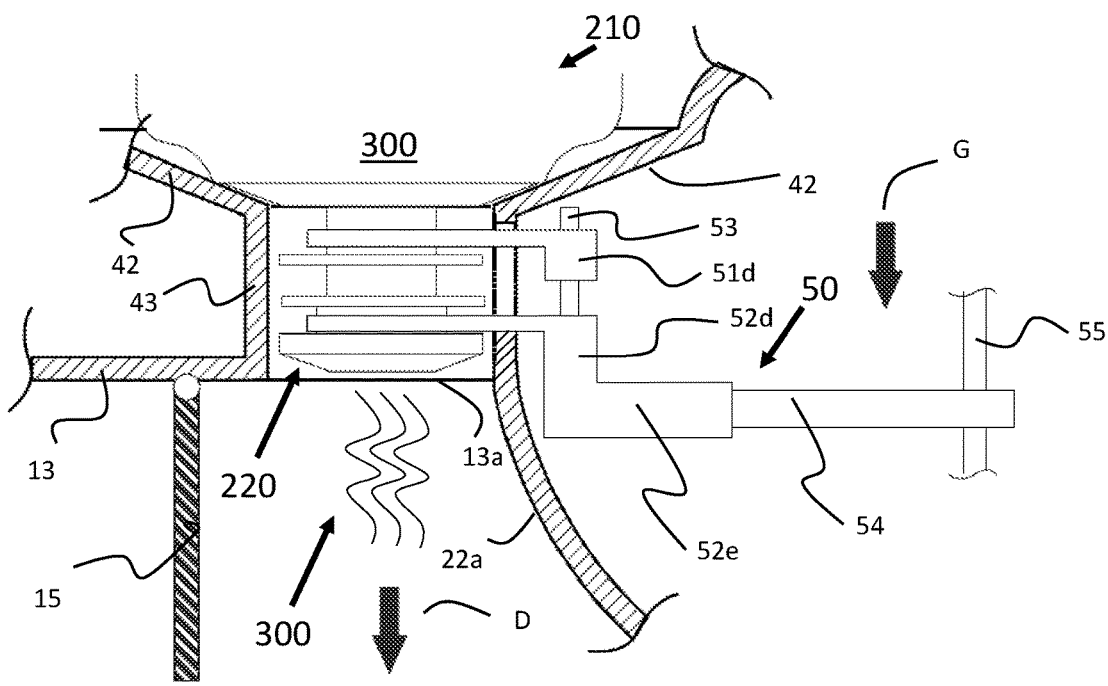
FIG. 42 is a magnified side elevation view, partly in cross-section and partly broken away, of the bottom portion of the receptacle vessel of the chamber portion of the present invention showing a push-pull valve in an open position; a valve actuation in an actuated, engagement position with the push-pull valve; the bottom door of the chamber portion in an open position, and a fluid flowing out of the flexible bag through the push-pull valve.

In FIG. 42, there is shown the bottom portion of the receptacle vessel 40 of the chamber portion 10. FIG. 42 further shows the valve actuation mechanism 50 in an actuated, engagement position with the flanges 225 and 228 of the push-pull valve 220 and the actuation mechanism 50 having moved in a downward vertical plane direction as indicated by arrow G. The bottom door 15 of the chamber portion 10 is in an open position, and fluid 300 is shown flowing out of the flexible bag 200 through the valve 220; the fluid 300 flowing in a downward vertical plane direction as indicated by arrow D.

Figure 43:
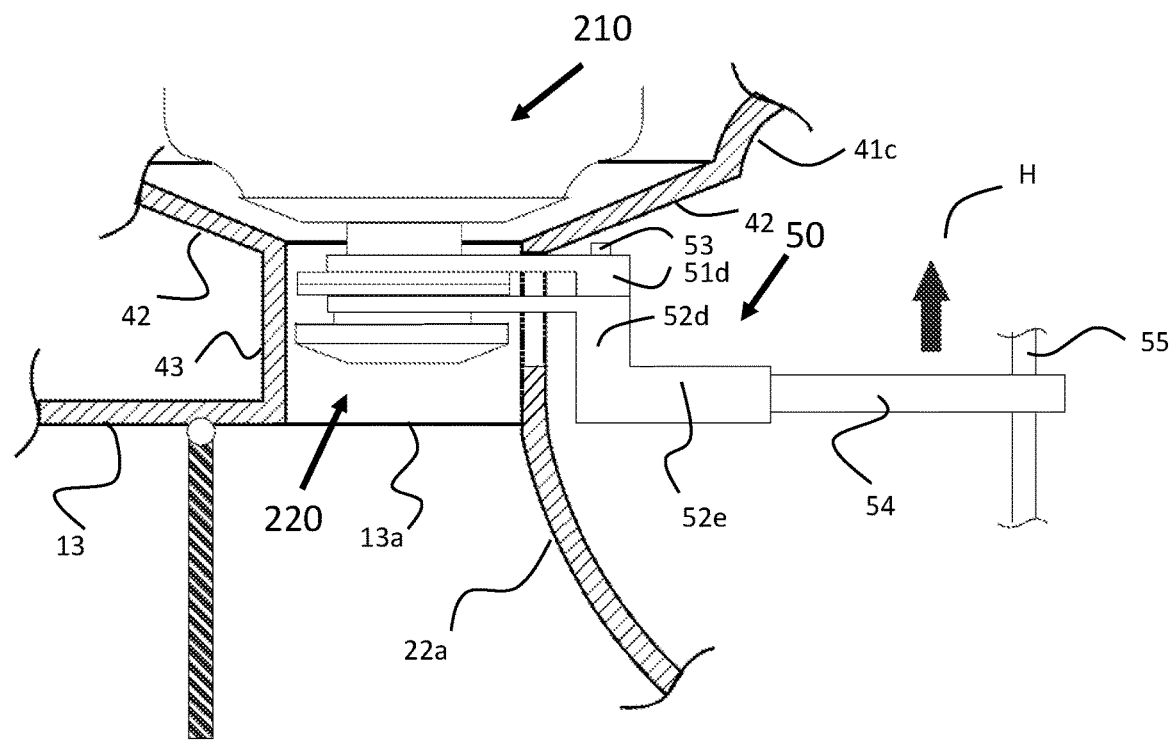
FIG. 43 is a magnified side elevation view, partly in cross-section and partly broken away, of the bottom portion of the receptacle vessel of the chamber portion of the present invention showing: a push-pull valve in a closed position; a valve actuation mechanism in an actuated, engagement position with the push-pull valve; the bottom door of the chamber portion in an open position, and no fluid flowing out of the closed flexible bag.

In FIG. 43, there is shown the bottom portion of the receptacle vessel 40 of the chamber portion 10. FIG. 43 further shows the push-pull valve 220 in a closed position after the valve actuation mechanism 50 is in an actuated, engagement position with the push-pull valve 220; and the actuation mechanism 50 has moved in an upward vertical plane direction as indicated by arrow H. The bottom door 15 of the chamber 10 is in an open position, and no fluid 300 is shown flowing out of the empty flexible bag 200.

Figure 44:
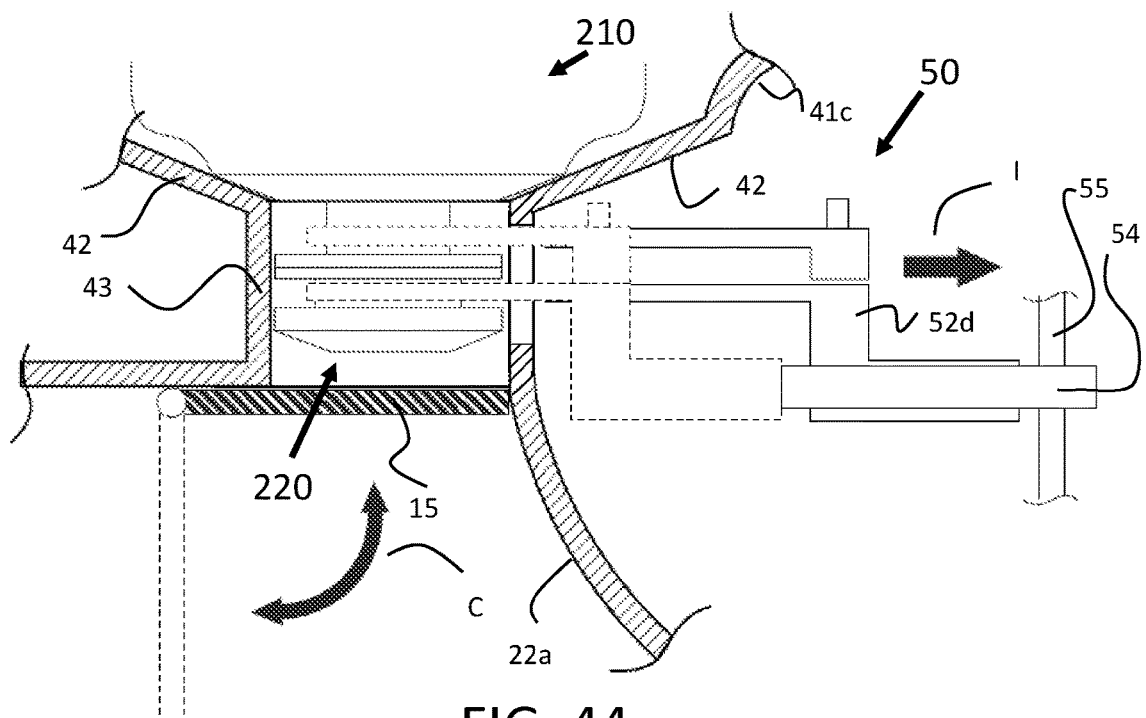
FIG. 44 is a magnified side elevation view, partly in cross-section and partly broken away, of the bottom portion of the receptacle vessel of the chamber portion of the present invention showing: a push-pull valve in a closed position; a valve actuation mechanism of in a retracted, non-actuated, non-engagement position relative to the push-pull valve; the bottom door of the chamber portion in a closed position; and no fluid flowing out of the closed flexible bag.

In FIG. 44 there is shown the bottom portion of the receptacle vessel 40 of the chamber portion 10. FIG. 44 further shows the push-pull valve 220 in a closed position; and the valve actuation mechanism 50 is in a retracted, non-actuated, non-engagement position with the valve 220 after the valve actuation mechanism 50 has moved in a horizontal plane direction as indicated by arrow I. The bottom door 15 of the chamber 10 in a closed position (the bottom door movable in the direction as indicated by arrow C), and no fluid 300 is shown flowing out of the empty flexible bag 200.

Figure 45:
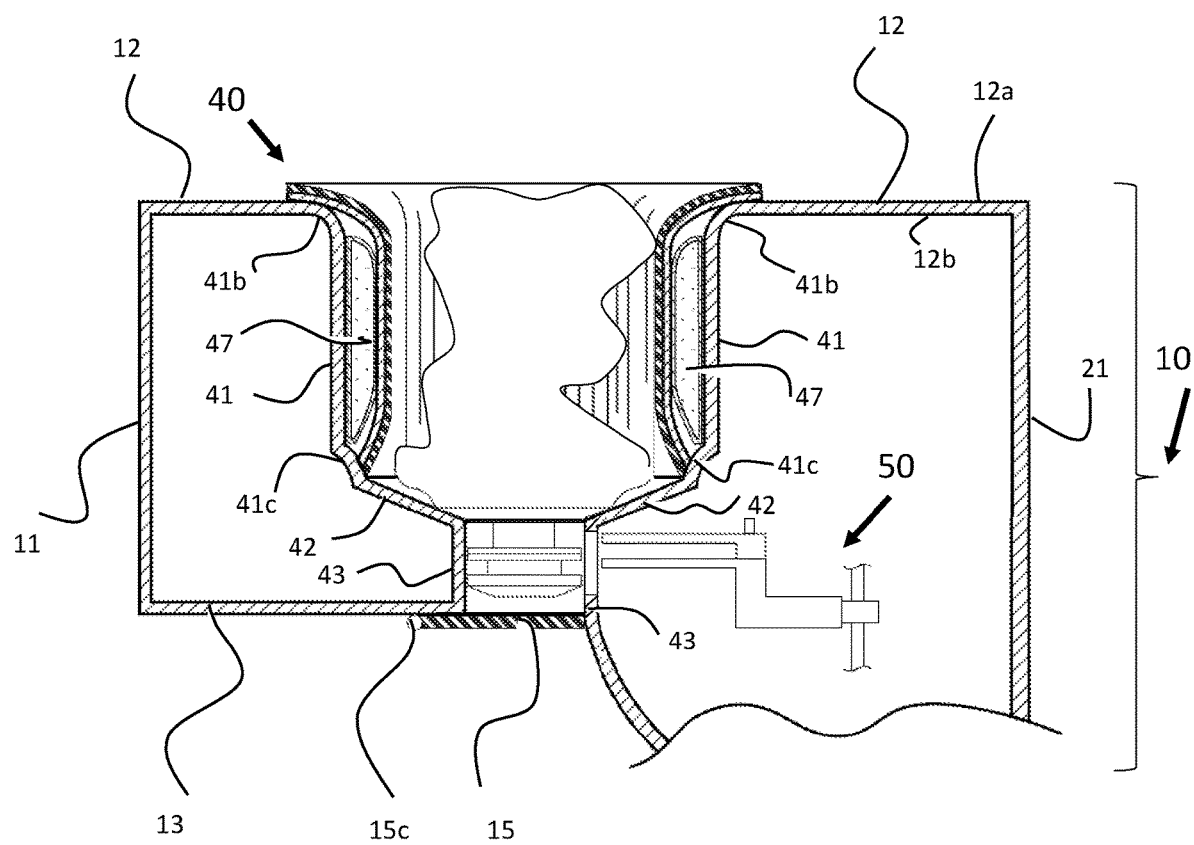
FIG. 45 is a side elevation view, partly in cross-section and partly broken away, of the chamber portion of the apparatus of the present invention without a lid showing a flexible bag emptied of its liquid fluid contents and disposed in the receptacle vessel of the chamber portion.

Once the fluid 300 inside the bag 200 has been dispensed and the bag 200 has been emptied of its contents, the bag 200 can be removed from the receptacle vessel 40 and out of the chamber 10 of the dispenser 100. With reference to FIG. 45, there is shown the chamber portion 10 of the dispenser 100 including a flexible bag 200 emptied of its liquid fluid contents; the empty bag 200 disposed in the receptacle vessel 40 of the chamber portion 10 without a lid 14; an inflated air bladder 46; the push-pull valve 220 in a closed position; the valve actuation mechanism 50 resting in a retracted, non-actuated, non-engagement position with the push-pull valve 220; the bottom door 15 of the chamber portion 10 in a closed position; and no fluid 300 flowing out of the empty flexible bag 200.

Augmented Dispensing

After the push-pull valve 220 of the bag 200 in the vessel 40 of the chamber portion 10 is opened, the breastmilk 300 is dispensed from the bag 200 by gravitational force. However, gravity alone may be insufficient to dispense the entire volume of the breastmilk 300 from the bag 200 or the breastmilk 300 may not dispense fast enough to fill the baby bottle 400 and to quickly feed a crying baby for example. Thus, in accordance with another optional embodiment of the present invention, a dual partitioned bladder configuration (not shown) having a first upper cell and a second lower cell may be useful for completely dispensing the entire volume of the breastmilk 300 of the bag 200. For example, by increasing the volume of air in the first upper cell compared to the second lower cell, the top of the bag 200 has a higher contact pressure than the bottom of the bag 200; and therefore, the breastmilk 300 toward the top of the bag 200 is pushed toward the bottom of the bag 200, into the open valve 220, and through the dispensing orifice 13*a* of wall 13 thereby forcing the breastmilk 300 at the top and bottom of the bag 300 out of the breastmilk bag 200.

Second Container

Once the breastmilk 300 is thawed or warmed to the serving temperature, the breastmilk 300 can be dispensed from the present invention breastmilk dispenser 100 directly into the second container 400 such as a standard rigid tubular baby bottle 400 so that the breastmilk 300 can be fed to an infant from the baby bottle 400.

In general, the amount of liquid fluid 300 to be dispensed by the dispenser 100 during the operation of the dispenser 100 can be preset for any quantity as desired for the selected fluid to be dispensed. For example, coffee may be dispensed at about 5 fluid ounces to provide a cup of coffee versus an amount of a juice beverage can be dispensed at about 4 fluid ounces. The amount of breastmilk 300 contained in the breastmilk bag 200 to be dispensed may be sufficient to fill a baby bottle 400 or less as desired. For example, the bag 200 useful in the present invention can be typically from about 5 fluid ounces (US fl oz; 148 milliters (mL)) to about 8 fl oz (237 mL) or any sufficient size to provide a volume of breastmilk to fill the capacity of a desired container and the amount of breastmilk desired to be fed to an infant.

Figure 2:
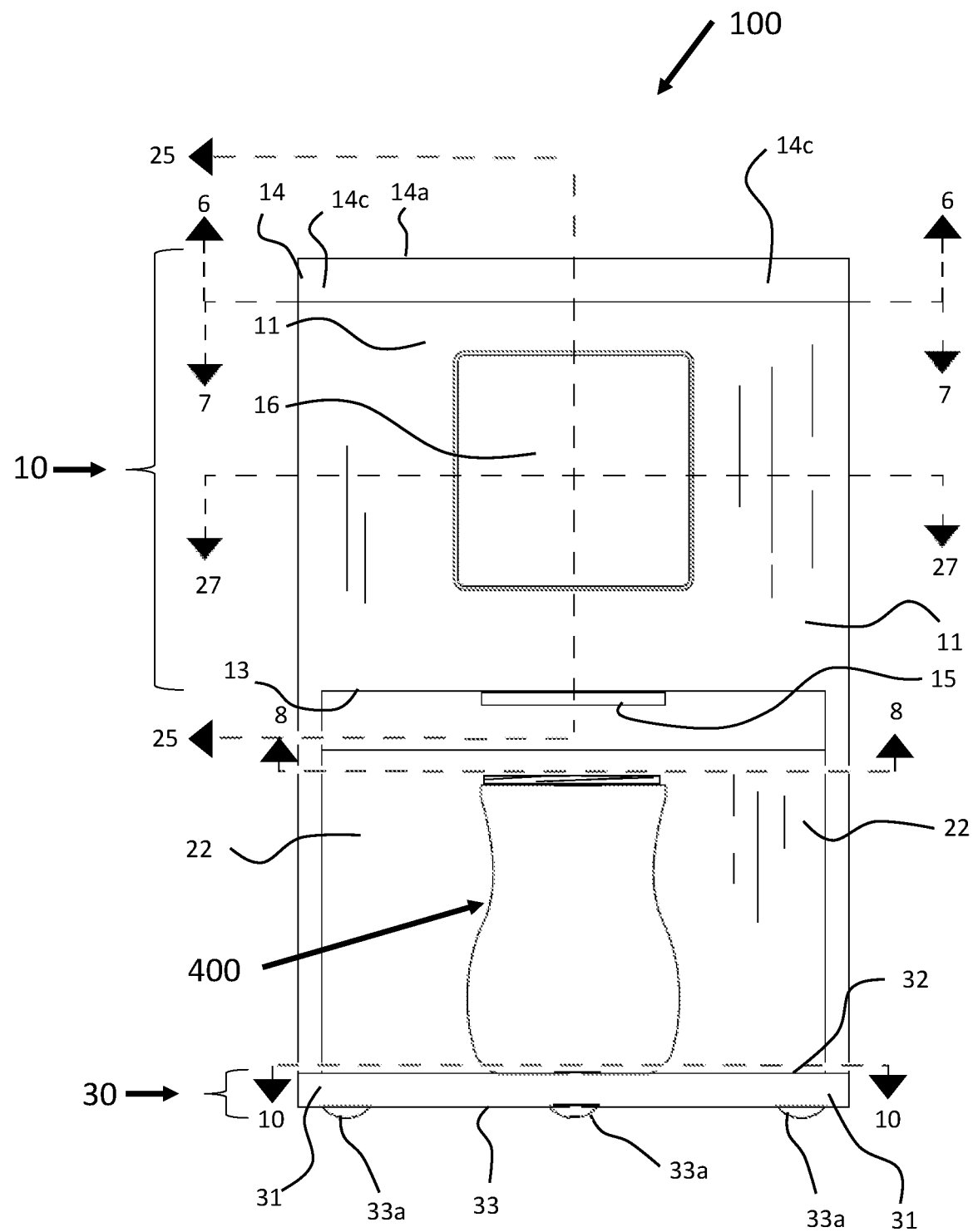
FIG. 2 is a front elevation view of the apparatus of the present invention shown in FIG. 1.
Figure 3:
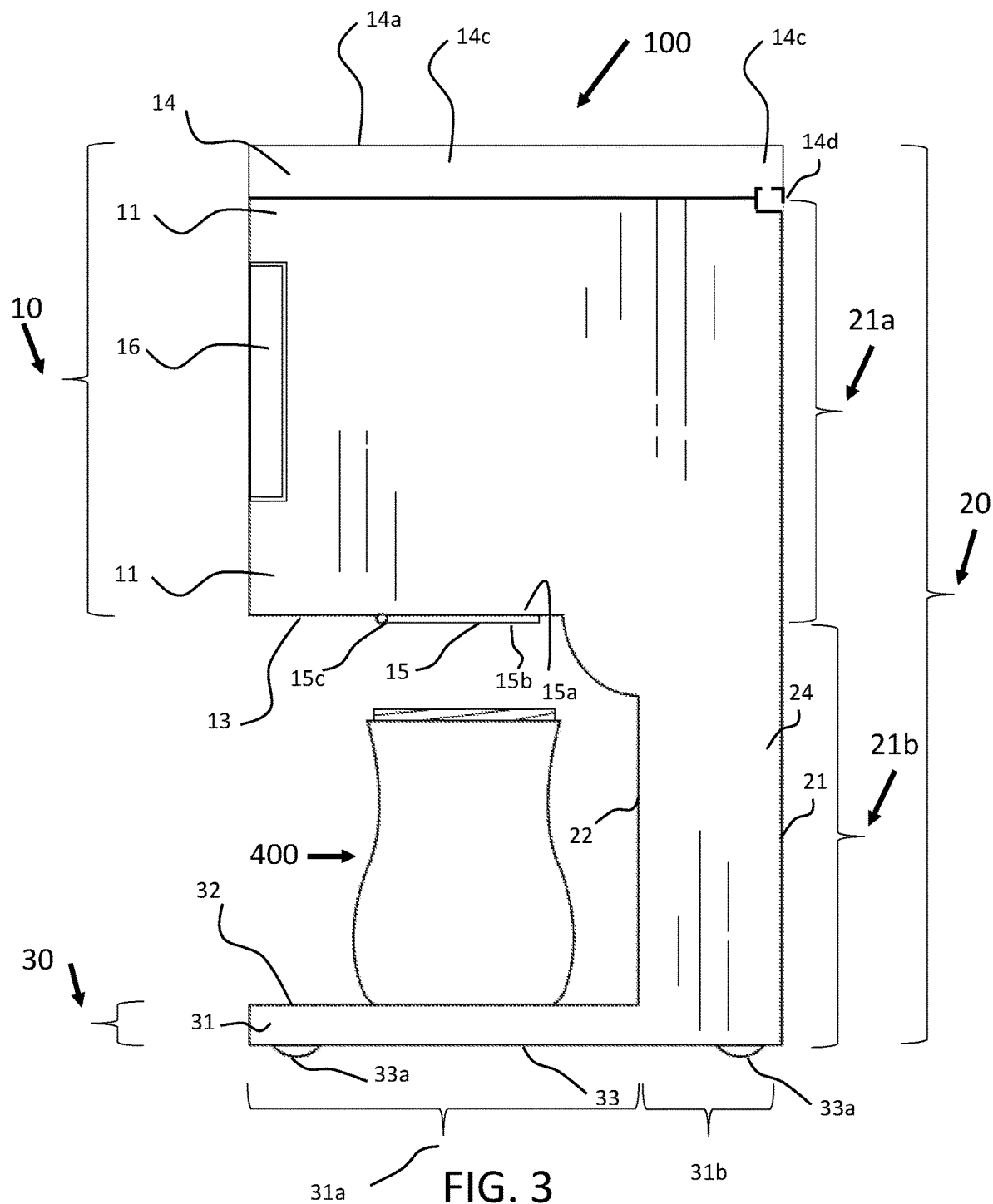
FIG. 3 is a side elevation view of the apparatus of the present invention shown in FIG. 1.
Figure 4:
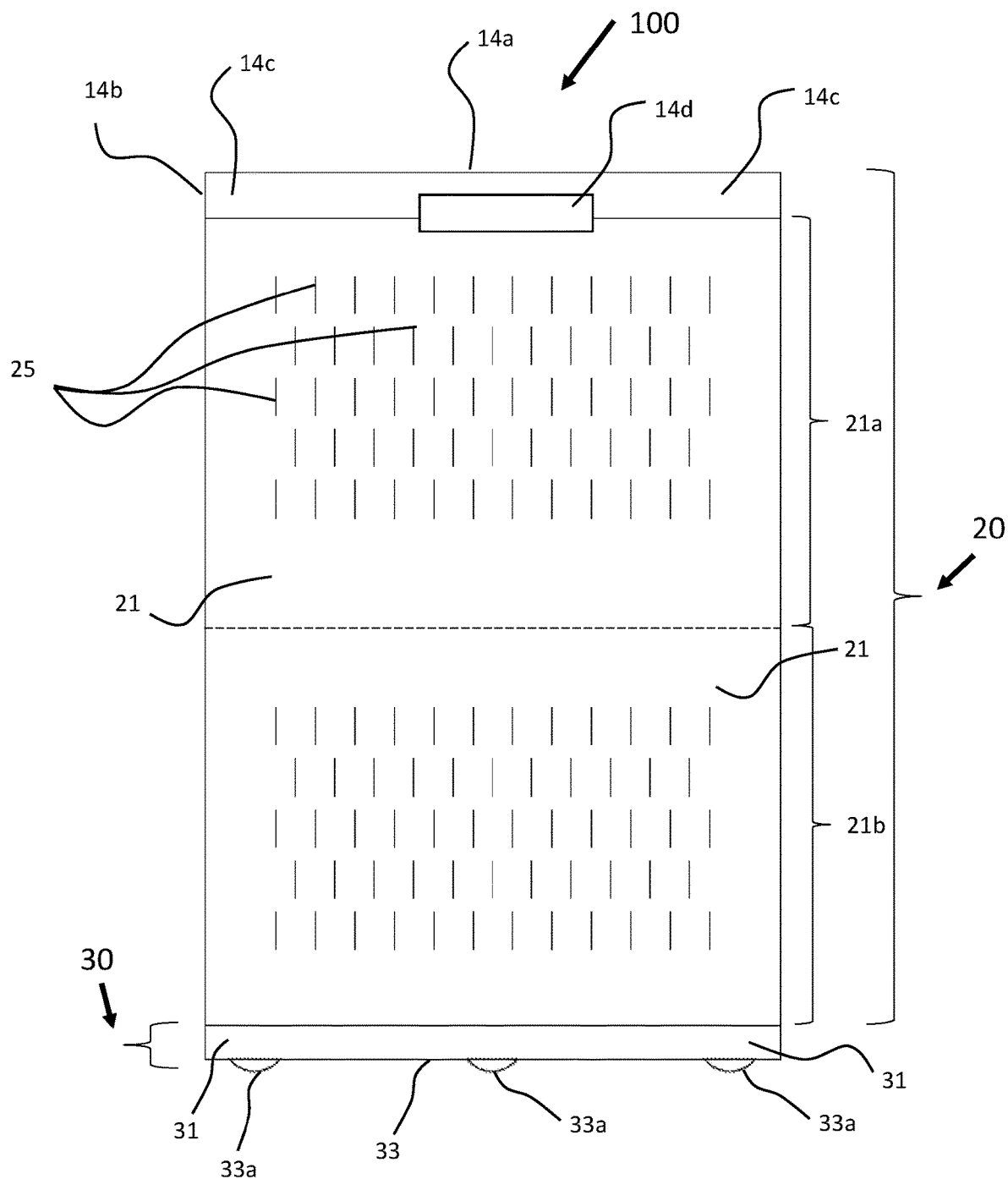
FIG. 4 is a back elevation view of the apparatus of the present invention shown in FIG. 1.
Figure 5:
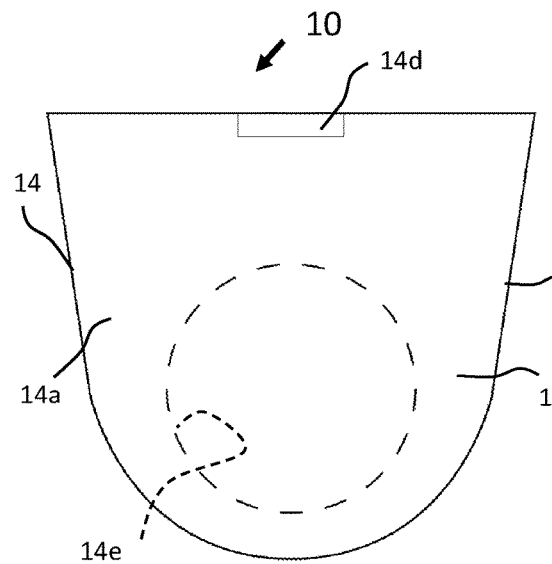
FIG. 5 is a top elevation view showing the top surface of a lid of the apparatus of the present invention shown in FIG. 1.

With reference to FIGS. 1-3, there is shown the second container 400 (different from the first container or bag 200) which can be for example a baby bottle 400. The baby bottle 400 useful in the present invention can be any baby bottle of a type intended for use and reuse in oral feeding breastmilk or baby formula to an infant. Such baby bottles are well known in the art and include a wide variety of infant oral feeding baby bottles currently on the market.

In general, the components of a conventional baby bottle 400 (also referred to herein as an infant feeding system or a baby feeding system) comprises a feed container 400, which is usually transparent and constructed of glass or of an equivalent rigid synthetic resinous material (i.e., plastic) capable of being washed and sterilized. The glass or plastic feed container 400 usually has a body 401 with a neck portion 402 at the container's opening end with an attachment means such as a male screw thread member 403 about the neck 402 which is adapted for releasably connecting a feed dispensing means (not shown). The feed dispensing means is usually a teat/nipple formed of rubber or plastic material and a female threaded retaining collar used to connect the feed dispensing means to the container 400. Thus, a baby bottle feeding system typically includes a container 400 comprising an elongated hollow cylindrical vessel constituted by an integral side wall and a bottom end wall, an externally threaded opening at the opposite (top) end from the bottom end wall, a feeding nipple, and a screw-on top collar for securing the nipple to the container. Typically, a universal threading 403 is integral to the neck 402 to allow for usage and interchangeability of a cap with a nipple. The universal cap/nipple is generally available as an off-the-shelf item.

In one embodiment, the second container 400 can be reusable such as the cylindrical vessel defining the container and the nipple of a conventional baby bottle described in U.S. Pat. No. 7,632,457, incorporated herein by reference. In another embodiment, the second container 400 can be disposable and non-reusable such as the baby bottle described in U.S. Pat. No. 6,138,847, incorporated herein by reference. In still another embodiment, the infant feeding system described in U.S. Patent Application Publication No. US2014/0107608A1, incorporated herein by reference, can be used as the second container 400 of the present invention.

Other Optional Embodiments

In still another preferred embodiment, the dispenser 100 may also be portable to provide a device, a machine or an appliance than can be placed on a planar (flat) surface such as a kitchen countertop for use in the kitchen or a table or other substantially planar surface. Once the dispenser 100 is in position at the desired location, the dispenser 100 is ready for use.

The breastmilk dispenser 100 of the present invention may include various optional structural features (not shown) without taking away from the overall design and function of the breastmilk dispenser. For example, in one embodiment of the breastmilk dispenser 100 of the present invention, the breastmilk dispenser 100 may include a mechanism (not shown) for controlling the volume of fluid dispensed from the first container 200. For instance, if the first container 200 contains 5 fluid ounces of breastmilk, the machine of the present invention may be used to dispense a user-selected portion of the 5 fluid-ounce content of the first container such as for example dispensing a 2-ounce portion in the second container 400 and leaving a 3-ounce portion of breastmilk in the first container 200.

In another embodiment, the breastmilk dispenser of the present invention may include an optional handle (not shown) for moving the dispenser 100. For example, the handle may be integral with the chamber portion 10, the compartment portion 20 and/or the base portion 30 for gripping the breastmilk dispenser and carrying the breastmilk dispenser to a different surface site.

In yet another embodiment, the dispenser may include one or more displays or electronic elements (not shown) such as optional visible indicator lights that can be added to the dispenser to indicate, for example: (i) when the dispenser is at an "on" position, (ii) when the first container bag in the breastmilk dispenser is empty of breastmilk, and/or (iii) when the first container bag is at a predetermined temperature and ready for dispensing. Buttons, toggle switches or other actuation members (not shown) can also be added to the walls of the chamber portion 10, the compartment portion 20 and/or the base portion 30 to activate the functions shown in the display as described above. Other optional structural, mechanical or logical embodiments, features, elements, or pieces may be added to the dispenser without departing from the spirit and scope of the present invention.

In other embodiments, the breastmilk dispenser 100 of the present invention may be useful in various commercial establishments such as day care facilities, restaurants, offices, and the like. For example, many children day-care establishments require parents to bring pre-made baby bottles each day for infants because the day care establishments may lack the required facilities and equipment to prepare bottles from frozen breastmilk. The present invention dispenser apparatus 100 and its method of use may be: (1) useful in such commercial establishments; (2) acceptable to passing regulatory sanitary specifications; and (3) readily approved by regulatory authority for the use of the present invention in such aforementioned commercial establishments.

It will become apparent to those skilled in the art that the present invention apparatus and method can be useful for preparing, storing, and dispensing any number of different flowable fluids for different end uses and applications. Accordingly, the apparatus and method of the present invention are not to be limited by the illustrative embodiments described above. Rather, the above-described embodiments of the present invention are considered as illustrative only of the principles of the present invention. As emphasized herein, the above-described embodiments of the present invention, particularly any "preferred" embodiments such as those directed to a portable apparatus and a method for use in storing, cooling, heating, and dispensing breastmilk, are merely possible examples of implementations, and are merely set forth for a clear understanding of the principles of the present invention. Further, numerous variations of the above-described embodiments of the present invention will readily occur to those skilled in the art. However, the present invention is not to be limited to the exact construction and operation shown in the drawings and described above. Many modifications may be made to the above-described embodiments of the present invention without departing substantially from the spirit and principles of the present invention. All such modifications and variations are intended to be included herein within the scope of this disclosure and the present invention and protected by the following claims. Accordingly, all suitable modifications and equivalents fall within the scope of the present invention as claimed.

What is claimed is:

1. A process of preparing breastmilk for feeding a baby on-demand by a caregiver comprising the steps of:
    (I) providing a portable apparatus adapted for storing, preparing and dispensing a supply of fluid liquid of breastmilk in a non-invasive and non-contaminating manner; said apparatus comprising:
        (a) a housing including a chamber portion having a top surface and bottom surface;
        (b) a housing including a machine compartment portion;
        (c) a support base portion having a top surface and a bottom surface;
        wherein the machine compartment portion is integral to the chamber portion and the base portion forming a space in a vertical plane direction between the top surface of the support base portion and the bottom surface of the chamber portion;
        (d) a receptacle vessel integrally disposed in said chamber portion; wherein said vessel is adapted for receiving a first container containing therein a predetermined volume of fluid liquid of breastmilk;
        (d1) a cooling means disposed in said compartment portion; wherein said cooling means is adapted for cooling the chamber portion to a preselected first temperature and maintaining the first container in the chamber portion at the first temperature for a period of time until the fluid liquid of breastmilk is ready to be dispensed from the apparatus and used; and/or
        (d2) a heating means disposed in said compartment portion; wherein said heating means is adapted for heating the chamber portion to a preselected second temperature and warming, defrosting or thawing the fluid liquid of breastmilk contained in the first container to the second temperature for a period of time until the fluid liquid of breastmilk is ready to be dispensed from the apparatus and used; and
        (e) a means for transferring, in a noninvasive and non-contaminating manner, a preselected volume of fluid liquid of breastmilk contained in the first container disposed in the receptacle vessel of said chamber portion, from said first container into a second container; wherein the second container is disposed in the space between the support base portion and underneath the chamber portion;
    (II) providing a frozen or refrigerated flexible bag, as the first container, containing frozen or refrigerated breastmilk;
    (III) placing the frozen or refrigerated flexible bag containing the frozen or refrigerated breastmilk into the portable apparatus of step (I);
    (IV) warming the frozen or refrigerated breastmilk in the flexible bag by heating the flexible bag using a heating means in the portable apparatus to a predetermined proper temperature that is safe for feeding a baby without burning or injuring the baby; and
    (V) dispensing the preselected volume of fluid liquid of breastmilk from the flexible bag in the receptacle vessel of the chamber portion via an orifice in the chamber portion and a reclosable door in an open position into a baby bottle, as the second container, adapted for use in feeding a baby.

2. The process of claim 1, wherein the flexible bag includes a reclosable valve having a reclosable opening therein in fluid communication with the fluid liquid of breastmilk of the flexible bag when the valve is in the open position; and wherein the dispensing step (V) includes the step of actuating, in a non-invasive manner, the valve of the flexible bag into an open position such that the fluid liquid of breastmilk in the flexible bag flows through the opening in the valve to allow the fluid liquid of breastmilk of the flexible bag to flow out of the flexible bag.

* * * * *